(12) United States Patent
Wolf et al.

(10) Patent No.: US 12,239,385 B2
(45) Date of Patent: Mar. 4, 2025

(54) UNIVERSAL TOOL ADAPTER

(71) Applicant: AUGMEDICS LTD., Yokneam Illit (IL)

(72) Inventors: Stuart Wolf, Yokneam (IL); Nissan Elimelech, Beerotaim (IL); Tomer Gera, Kfar—Tavor (IL)

(73) Assignee: AUGMEDICS LTD., Yokneam Illit (IL)

( * ) Notice: Subject to any disclaimer, the term of this patent is extended or adjusted under 35 U.S.C. 154(b) by 1128 days.

(21) Appl. No.: 17/015,199

(22) Filed: Sep. 9, 2020

(65) Prior Publication Data

US 2022/0071712 A1    Mar. 10, 2022

(51) Int. Cl.
| | | |
|---|---|---|
| A61B 34/20 | (2016.01) | |
| A61B 17/00 | (2006.01) | |
| A61B 17/88 | (2006.01) | |
| A61B 90/00 | (2016.01) | |

(52) U.S. Cl.
CPC .......... *A61B 34/20* (2016.02); *A61B 17/8875* (2013.01); *A61B 90/03* (2016.02); *A61B 90/39* (2016.02); *A61B 2017/00486* (2013.01); *A61B 2034/2055* (2016.02); *A61B 2090/031* (2016.02); *A61B 2090/3937* (2016.02); *A61B 2090/3983* (2016.02)

(58) Field of Classification Search
CPC ..... A61B 34/20; A61B 17/8875; A61B 90/03; A61B 90/39; A61B 2017/00486; A61B 2034/2055; A61B 2090/031; A61B 2090/3937; A61B 2090/3983; A61B 90/361; A61B 2017/00477; A61B 2090/365; A61B 2090/371; A61B 2090/372; A61B 2090/502; G02B 27/017
See application file for complete search history.

(56) References Cited

U.S. PATENT DOCUMENTS

| | | |
|---|---|---|
| 3,690,776 A | 9/1972 | Zaporoshan |
| 4,459,358 A | 7/1984 | Berke |
| 4,711,512 A | 12/1987 | Upatnieks |
| 4,863,238 A | 9/1989 | Brewster |

(Continued)

FOREIGN PATENT DOCUMENTS

| | | |
|---|---|---|
| CA | 3022448 A1 | 2/2018 |
| CA | 3034314 A1 | 2/2018 |

(Continued)

OTHER PUBLICATIONS

US 11,395,705 B2, 09/2022, Lang (withdrawn)

(Continued)

*Primary Examiner* — Brian T Gedeon
*Assistant Examiner* — Rumaisa Rashid Baig
(74) *Attorney, Agent, or Firm* — KNOBBE, MARTENS, OLSON & BEAR, LLP

(57) ABSTRACT

A tool adapter, consisting of an adapter arm having a proximal end terminating with a connection and a distal end having a circular coupling, the circular coupling having a center and defining an axis orthogonal to the circular coupling and passing through the center. The adapter also has a tool grip rotatingly connected to the circular coupling so as to permit rotation of the tool grip about the axis, the tool grip being configured to fixedly retain a tool along the axis.

21 Claims, 7 Drawing Sheets

(56) References Cited

U.S. PATENT DOCUMENTS

| | | |
|---|---|---|
| 4,944,739 A | 7/1990 | Torre |
| 5,100,420 A * | 3/1992 | Green ............... A61B 17/1285 |
| | | 227/19 |
| 5,357,292 A | 10/1994 | Wiedner |
| 5,410,802 A * | 5/1995 | Buckley ................. H01R 43/20 |
| | | 29/760 |
| 5,441,042 A * | 8/1995 | Putman ................... B25J 9/042 |
| | | 600/102 |
| 5,442,146 A | 8/1995 | Bell |
| 5,510,832 A | 4/1996 | Garcia |
| D370,309 S | 5/1996 | Stucky |
| 5,620,188 A * | 4/1997 | McCurry .............. B23B 31/202 |
| | | 409/234 |
| 5,636,255 A | 6/1997 | Ellis |
| 5,665,092 A | 9/1997 | Mangiardi et al. |
| 5,743,731 A * | 4/1998 | Lares ................... A61B 1/0607 |
| | | 433/29 |
| 5,771,121 A | 6/1998 | Hentschke |
| 5,792,046 A | 8/1998 | Dobrovolny |
| 5,841,507 A | 11/1998 | Barnes et al. |
| 6,006,126 A | 12/1999 | Cosman |
| 6,038,467 A | 3/2000 | De Bliek et al. |
| 6,125,164 A | 9/2000 | Murphy |
| 6,138,530 A * | 10/2000 | McClure .............. B25B 13/488 |
| | | 81/58 |
| 6,147,805 A | 11/2000 | Fergason |
| 6,227,667 B1 | 5/2001 | Halldorsson |
| 6,256,529 B1 | 7/2001 | Holupka et al. |
| 6,285,505 B1 | 9/2001 | Melville et al. |
| 6,314,310 B1 | 11/2001 | Ben-Haim et al. |
| 6,349,001 B1 | 2/2002 | Spitzer |
| 6,444,192 B1 | 9/2002 | Mattrey |
| 6,449,090 B1 | 9/2002 | Omar |
| 6,456,405 B2 | 9/2002 | Horikoshi et al. |
| 6,456,868 B2 | 9/2002 | Saito et al. |
| 6,474,159 B1 | 11/2002 | Foxlin et al. |
| 6,518,939 B1 | 2/2003 | Kikuchi |
| 6,527,777 B2 | 3/2003 | Justin |
| 6,529,331 B2 | 3/2003 | Massof et al. |
| 6,549,645 B1 | 4/2003 | Oikawa |
| 6,578,962 B1 | 6/2003 | Amir et al. |
| 6,609,022 B2 | 8/2003 | Vilsmeier et al. |
| 6,610,009 B2 | 8/2003 | Person |
| D480,476 S | 10/2003 | Martinson et al. |
| 6,659,611 B2 | 12/2003 | Amir et al. |
| 6,675,040 B1 | 1/2004 | Cosman |
| 6,683,584 B2 | 1/2004 | Ronzani et al. |
| 6,690,964 B2 | 2/2004 | Bieger et al. |
| 6,714,810 B2 | 3/2004 | Grzeszczuk et al. |
| 6,737,425 B1 | 5/2004 | Yamamoto |
| 6,740,882 B2 | 5/2004 | Weinberg |
| 6,757,068 B2 | 6/2004 | Foxlin |
| 6,759,200 B1 | 7/2004 | Stanton |
| 6,847,336 B1 | 1/2005 | Lemelson et al. |
| 6,856,324 B2 | 2/2005 | Sauer |
| 6,856,826 B2 | 2/2005 | Seeley et al. |
| 6,891,518 B2 | 5/2005 | Sauer et al. |
| 6,900,777 B1 | 5/2005 | Hebert et al. |
| 6,919,867 B2 | 7/2005 | Sauer |
| 6,921,167 B2 | 7/2005 | Nagata |
| 6,966,668 B2 | 11/2005 | Cugini |
| 6,980,849 B2 | 12/2005 | Sasso |
| 6,993,374 B2 | 1/2006 | Sasso |
| 6,997,552 B1 | 2/2006 | Hung |
| 6,999,239 B1 | 2/2006 | Martins et al. |
| 7,000,262 B2 | 2/2006 | Bielefeld |
| 7,035,371 B2 | 4/2006 | Boese et al. |
| 7,043,961 B2 | 5/2006 | Pandey et al. |
| 7,072,435 B2 | 7/2006 | Metz et al. |
| 7,103,233 B2 | 9/2006 | Stearns |
| 7,107,091 B2 | 9/2006 | Jutras et al. |
| 7,112,656 B2 | 9/2006 | Desnoyers |
| 7,141,812 B2 | 11/2006 | Appleby |
| 7,157,459 B2 | 1/2007 | Ohta |
| 7,169,785 B2 | 1/2007 | Timmer |
| 7,171,255 B2 | 1/2007 | Holupka et al. |
| 7,176,936 B2 | 2/2007 | Sauer et al. |
| 7,187,792 B2 | 3/2007 | Fu |
| 7,190,331 B2 | 3/2007 | Genc et al. |
| 7,194,295 B2 | 3/2007 | Vilsmeier |
| 7,215,322 B2 | 5/2007 | Genc et al. |
| 7,229,078 B2 | 6/2007 | Lechot |
| 7,231,076 B2 | 6/2007 | Fu |
| 7,235,076 B2 | 6/2007 | Pacheco |
| 7,239,330 B2 | 7/2007 | Sauer et al. |
| 7,259,266 B2 | 8/2007 | Carter |
| 7,260,426 B2 | 8/2007 | Schweikard |
| 7,269,192 B2 | 9/2007 | Hayashi |
| 7,281,826 B2 | 10/2007 | Huang |
| 7,315,636 B2 | 1/2008 | Kuduvalli |
| 7,320,556 B2 | 1/2008 | Vagn-Erik |
| 7,330,578 B2 | 2/2008 | Wang |
| 7,359,535 B2 | 4/2008 | Salla |
| 7,364,314 B2 | 4/2008 | Nilsen et al. |
| 7,366,934 B1 | 4/2008 | Narayan et al. |
| 7,379,077 B2 | 5/2008 | Bani-Hashemi |
| 7,431,453 B2 | 10/2008 | Hogan |
| 7,435,219 B2 | 10/2008 | Kim |
| 7,450,743 B2 | 11/2008 | Sundar et al. |
| 7,458,977 B2 | 12/2008 | McGinley |
| 7,462,852 B2 | 12/2008 | Appleby |
| 7,493,153 B2 | 2/2009 | Ahmed et al. |
| 7,505,617 B2 | 3/2009 | Fu |
| 7,507,968 B2 | 3/2009 | Wollenweber |
| 7,518,136 B2 | 4/2009 | Appleby |
| 7,525,735 B2 | 4/2009 | Sottilare et al. |
| D592,691 S | 5/2009 | Chang |
| D592,692 S | 5/2009 | Chang |
| D592,693 S | 5/2009 | Chang |
| 7,536,216 B2 | 5/2009 | Geiger et al. |
| 7,542,791 B2 | 6/2009 | Mire et al. |
| 7,556,428 B2 | 7/2009 | Sukovic et al. |
| 7,557,824 B2 | 7/2009 | Holliman |
| 7,563,228 B2 | 7/2009 | Ma et al. |
| 7,567,834 B2 | 7/2009 | Clayton |
| 7,570,791 B2 | 8/2009 | Frank et al. |
| 7,586,686 B1 | 9/2009 | Hall |
| D602,620 S | 10/2009 | Cristoforo |
| 7,605,826 B2 | 10/2009 | Sauer |
| 7,606,613 B2 | 10/2009 | Simon et al. |
| 7,607,775 B2 | 10/2009 | Hermanson |
| 7,620,223 B2 | 11/2009 | Xu |
| 7,623,902 B2 | 11/2009 | Pacheco |
| 7,627,085 B2 | 12/2009 | Boyden et al. |
| 7,630,753 B2 | 12/2009 | Simon et al. |
| 7,633,501 B2 | 12/2009 | Wood |
| 7,645,050 B2 | 1/2010 | Wilt |
| 7,653,226 B2 | 1/2010 | Guhring et al. |
| 7,657,075 B2 | 2/2010 | Viswanathan |
| 7,689,019 B2 | 3/2010 | Boese |
| 7,689,042 B2 | 3/2010 | Brunner |
| 7,689,320 B2 | 3/2010 | Prisco |
| 7,699,486 B1 | 4/2010 | Beiner |
| 7,699,793 B2 | 4/2010 | Gotte |
| 7,719,769 B2 | 5/2010 | Sugihara et al. |
| D617,825 S | 6/2010 | Chang |
| 7,734,327 B2 * | 6/2010 | Colquhoun ............ A61B 90/39 |
| | | 600/407 |
| D619,285 S | 7/2010 | Cristoforo |
| 7,751,865 B2 | 7/2010 | Jascob et al. |
| 7,758,204 B2 | 7/2010 | Klipstein |
| 7,768,702 B2 | 8/2010 | Hirose et al. |
| 7,769,236 B2 | 8/2010 | Fiala |
| 7,773,074 B2 | 8/2010 | Arenson et al. |
| 7,774,044 B2 | 8/2010 | Sauer et al. |
| 7,822,483 B2 | 10/2010 | Stone et al. |
| D628,307 S | 11/2010 | Krause-Bonte |
| 7,826,902 B2 | 11/2010 | Stone et al. |
| 7,831,073 B2 | 11/2010 | Fu et al. |
| 7,831,096 B2 | 11/2010 | Williamson |
| 7,835,778 B2 | 11/2010 | Foley |
| 7,835,784 B2 | 11/2010 | Mire et al. |
| 7,837,987 B2 | 11/2010 | Shi |

(56) References Cited

U.S. PATENT DOCUMENTS

| | | |
|---|---|---|
| 7,840,093 B2 | 11/2010 | Fu et al. |
| 7,840,253 B2 | 11/2010 | Tremblay et al. |
| 7,840,256 B2 | 11/2010 | Lakin et al. |
| 7,853,305 B2 | 12/2010 | Simon |
| 7,854,705 B2 | 12/2010 | Pawluczyk |
| 7,857,271 B2 | 12/2010 | Lees |
| 7,860,282 B2 | 12/2010 | Boese |
| D630,766 S | 1/2011 | Harbin |
| 7,865,269 B2 | 1/2011 | Prisco |
| 7,874,686 B2 | 1/2011 | Rossner et al. |
| 7,881,770 B2 | 2/2011 | Melkent et al. |
| 7,893,413 B1 | 2/2011 | Appleby |
| 7,894,649 B2 | 2/2011 | Fu |
| 7,920,162 B2 | 4/2011 | Masini et al. |
| 7,922,391 B2 | 4/2011 | Essenreiter et al. |
| 7,938,553 B1 | 5/2011 | Beiner |
| 7,945,310 B2 | 5/2011 | Gattani |
| 7,953,471 B2 | 5/2011 | Clayton |
| 7,969,383 B2 | 6/2011 | Eberl et al. |
| 7,974,677 B2 | 7/2011 | Mire et al. |
| 7,985,756 B2 | 7/2011 | Barlow |
| 7,991,557 B2 | 8/2011 | Liew |
| 7,993,353 B2 | 8/2011 | Robner et al. |
| 7,996,064 B2 | 8/2011 | Simon et al. |
| 8,004,524 B2 | 8/2011 | Deinzer |
| 8,021,300 B2 | 9/2011 | Ma et al. |
| 8,022,984 B2 | 9/2011 | Cheong |
| 8,045,266 B2 | 10/2011 | Nakamura |
| 8,060,181 B2 | 11/2011 | Ponce |
| 8,068,581 B2 | 11/2011 | Boese et al. |
| 8,068,896 B2 | 11/2011 | Daghighian |
| 8,077,943 B2 | 12/2011 | Wiliams |
| 8,079,957 B2 | 12/2011 | Ma et al. |
| 8,081,812 B2 | 12/2011 | Kreiser |
| 8,085,075 B2 | 12/2011 | Huffman |
| 8,085,897 B2 | 12/2011 | Morton |
| 8,090,175 B2 | 1/2012 | Fu |
| 8,092,400 B2 | 1/2012 | Warkentine |
| 8,108,072 B2 | 1/2012 | Zhao |
| 8,112,292 B2 | 2/2012 | Simon |
| 8,116,847 B2 | 2/2012 | Gattani et al. |
| 8,120,847 B2 | 2/2012 | Chang |
| 8,121,255 B2 | 2/2012 | Sugiyama |
| 8,155,479 B2 | 4/2012 | Hoffman |
| 8,180,132 B2 | 5/2012 | Gorges et al. |
| 8,180,429 B2 | 5/2012 | Sasso |
| 8,208,599 B2 | 6/2012 | Ye |
| 8,216,211 B2 | 7/2012 | Mathis et al. |
| 8,221,402 B2 | 7/2012 | Francischelli |
| 8,239,001 B2 | 8/2012 | Verard et al. |
| 8,244,012 B2 | 8/2012 | Liang et al. |
| 8,253,778 B2 | 8/2012 | Atsushi |
| 8,271,069 B2 | 9/2012 | Jascob et al. |
| 8,280,491 B2 | 10/2012 | Kuduvalli et al. |
| 8,285,021 B2 | 10/2012 | Boese |
| 8,300,315 B2 | 10/2012 | Kobayashi |
| 8,305,685 B2 | 11/2012 | Heine |
| 8,306,305 B2 | 11/2012 | Porat et al. |
| 8,309,932 B2 | 11/2012 | Haselman |
| 8,317,320 B2 | 11/2012 | Huang |
| 8,328,815 B2 | 12/2012 | Farr et al. |
| 8,335,553 B2 | 12/2012 | Rubner |
| 8,335,557 B2 | 12/2012 | Maschke |
| 8,340,379 B2 | 12/2012 | Razzaque et al. |
| 8,369,925 B2 | 2/2013 | Giesel |
| 8,386,022 B2 | 2/2013 | Jutras et al. |
| 8,394,144 B2 | 3/2013 | Zehavi |
| 8,398,541 B2 | 3/2013 | Dimaio et al. |
| 8,444,266 B2 | 5/2013 | Waters |
| 8,457,719 B2 | 6/2013 | Moctezuma De La Barrera et al. |
| 8,467,851 B2 | 6/2013 | Mire et al. |
| 8,469,902 B2 | 6/2013 | Dick |
| 8,475,470 B2 | 7/2013 | Von Jako |
| 8,494,612 B2 | 7/2013 | Vetter et al. |
| 8,509,503 B2 | 8/2013 | Nahum et al. |
| 8,511,827 B2 | 8/2013 | Hua et al. |
| 8,531,394 B2 | 9/2013 | Maltz |
| 8,540,364 B2 | 9/2013 | Waters |
| 8,545,012 B2 | 10/2013 | Waters |
| 8,548,567 B2 | 10/2013 | Maschke et al. |
| 8,556,883 B2 | 10/2013 | Saleh |
| 8,559,596 B2 | 10/2013 | Thomson |
| 8,567,945 B2 | 10/2013 | Waters |
| 8,571,353 B2 | 10/2013 | Watanabe |
| 8,585,598 B2 | 11/2013 | Razzaque et al. |
| 8,600,001 B2 | 12/2013 | Schweizer |
| 8,600,477 B2 | 12/2013 | Beyar |
| 8,605,199 B2 | 12/2013 | Imai |
| 8,611,988 B2 | 12/2013 | Miyamoto |
| 8,612,024 B2 | 12/2013 | Stone et al. |
| 8,634,897 B2 | 1/2014 | Simon |
| 8,641,621 B2 | 2/2014 | Razzaque et al. |
| 8,643,950 B2 | 2/2014 | König |
| 8,644,907 B2 | 2/2014 | Hartmann et al. |
| 8,674,902 B2 | 3/2014 | Park |
| 8,686,923 B2 | 4/2014 | Eberl et al. |
| 8,690,581 B2 | 4/2014 | Ruf et al. |
| 8,690,776 B2 | 4/2014 | Razzaque et al. |
| 8,692,845 B2 | 4/2014 | Fedorovskaya et al. |
| 8,693,632 B2 | 4/2014 | Allison |
| 8,694,075 B2 | 4/2014 | Groszmann |
| 8,699,765 B2 | 4/2014 | Hao |
| 8,705,829 B2 | 4/2014 | Frank |
| 8,737,708 B2 | 5/2014 | Hartmann et al. |
| 8,746,887 B2 | 6/2014 | Shestak |
| 8,764,025 B1 * | 7/2014 | Gao ............... B25B 23/0042 279/22 |
| 8,784,450 B2 | 7/2014 | Moskowitz et al. |
| 8,786,689 B1 | 7/2014 | Liu |
| D710,545 S | 8/2014 | Wu |
| D710,546 S | 8/2014 | Wu |
| 8,827,934 B2 | 9/2014 | Chopra et al. |
| 8,831,706 B2 | 9/2014 | Fu |
| 8,836,768 B1 | 9/2014 | Rafii et al. |
| 8,838,199 B2 | 9/2014 | Simon et al. |
| 8,848,977 B2 | 9/2014 | Bammer et al. |
| 8,855,395 B2 | 10/2014 | Baturin |
| 8,878,900 B2 | 11/2014 | Yang et al. |
| 8,879,815 B2 | 11/2014 | Miao et al. |
| 8,885,177 B2 | 11/2014 | Ben-Yishai et al. |
| 8,890,772 B2 | 11/2014 | Woo |
| 8,890,773 B1 | 11/2014 | Pederson |
| 8,890,943 B2 | 11/2014 | Lee |
| 8,897,514 B2 | 11/2014 | Feikas |
| 8,900,131 B2 | 12/2014 | Chopra et al. |
| 8,903,150 B2 | 12/2014 | Star-Lack |
| 8,908,952 B2 | 12/2014 | Isaacs et al. |
| 8,911,358 B2 | 12/2014 | Koninckx et al. |
| 8,917,268 B2 | 12/2014 | Johnsen |
| 8,920,776 B2 | 12/2014 | Gaiger |
| 8,922,589 B2 | 12/2014 | Laor |
| 8,941,559 B2 | 1/2015 | Bar-Zeev et al. |
| 8,942,455 B2 | 1/2015 | Chou |
| 8,950,877 B2 | 2/2015 | Northey et al. |
| 8,953,246 B2 | 2/2015 | Koenig |
| 8,961,500 B2 * | 2/2015 | Dicorleto ............... A61B 34/20 606/1 |
| 8,965,583 B2 | 2/2015 | Ortmaier et al. |
| 8,969,829 B2 | 3/2015 | Wollenweber |
| 8,989,349 B2 | 3/2015 | Thomson |
| 8,992,580 B2 | 3/2015 | Bar |
| 8,994,729 B2 | 3/2015 | Nakamura |
| 8,994,795 B2 | 3/2015 | Oh |
| 9,004,711 B2 | 4/2015 | Gerolemou |
| 9,005,211 B2 | 4/2015 | Brundobler et al. |
| 9,011,441 B2 | 4/2015 | Bertagnoli et al. |
| 9,057,759 B2 | 6/2015 | Klingenbeck |
| 9,060,757 B2 | 6/2015 | Lawson et al. |
| 9,066,751 B2 | 6/2015 | Sasso |
| 9,081,436 B1 | 7/2015 | Berme |
| 9,084,635 B2 | 7/2015 | Nuckley et al. |
| 9,085,643 B2 | 7/2015 | Svanborg |
| 9,087,471 B2 | 7/2015 | Miao |
| 9,100,643 B2 | 8/2015 | McDowall |

(56) References Cited

U.S. PATENT DOCUMENTS

| | | |
|---|---|---|
| 9,101,394 B2 | 8/2015 | Arata et al. |
| 9,104,902 B2 | 8/2015 | Xu et al. |
| 9,111,175 B2 | 8/2015 | Strommer |
| 9,123,155 B2 | 9/2015 | Cunningham et al. |
| 9,125,556 B2 | 9/2015 | Zehavi |
| 9,129,054 B2 | 9/2015 | Nawana et al. |
| 9,129,372 B2 | 9/2015 | Kriston |
| 9,132,361 B2 | 9/2015 | Smithwick |
| 9,135,706 B2 | 9/2015 | Zagorchev et al. |
| 9,141,873 B2 | 9/2015 | Takemoto |
| 9,142,020 B2 | 9/2015 | Deguise et al. |
| 9,149,317 B2 * | 10/2015 | Arthur .................. A61K 31/55 |
| 9,165,203 B2 | 10/2015 | McCarthy |
| 9,165,362 B2 | 10/2015 | Siewerdsen et al. |
| 9,179,984 B2 | 11/2015 | Teichman et al. |
| D746,354 S | 12/2015 | Chang |
| 9,208,916 B2 | 12/2015 | Appleby |
| 9,220,573 B2 | 12/2015 | Kendrick et al. |
| 9,225,895 B2 | 12/2015 | Kozinski |
| 9,232,982 B2 | 1/2016 | Soler et al. |
| 9,235,934 B2 | 1/2016 | Mandella |
| 9,240,046 B2 | 1/2016 | Carrell et al. |
| 9,244,278 B2 | 1/2016 | Sugiyama et al. |
| 9,247,240 B2 | 1/2016 | Park |
| 9,259,192 B2 | 2/2016 | Ishihara |
| 9,265,572 B2 | 2/2016 | Fuchs et al. |
| 9,269,192 B2 | 2/2016 | Kobayashi |
| 9,283,052 B2 | 3/2016 | Ponce |
| 9,286,730 B2 | 3/2016 | Bar-Zeev et al. |
| 9,289,267 B2 | 3/2016 | Sauer et al. |
| 9,300,949 B2 | 3/2016 | Ahearn |
| 9,305,354 B2 | 4/2016 | Burlon et al. |
| 9,310,591 B2 | 4/2016 | Hua et al. |
| 9,320,474 B2 | 4/2016 | Demri |
| 9,323,055 B2 | 4/2016 | Baillot |
| 9,330,477 B2 | 5/2016 | Rappel |
| 9,335,547 B2 | 5/2016 | Takano et al. |
| 9,335,567 B2 | 5/2016 | Nakamura |
| 9,341,704 B2 | 5/2016 | Picard |
| 9,344,686 B2 | 5/2016 | Moharir |
| 9,349,066 B2 | 5/2016 | Koo |
| 9,349,520 B2 | 5/2016 | Demetriou |
| 9,364,294 B2 | 6/2016 | Razzaque et al. |
| 9,370,332 B2 | 6/2016 | Paladini et al. |
| 9,373,166 B2 | 6/2016 | Azar |
| 9,375,639 B2 | 6/2016 | Kobayashi et al. |
| 9,378,558 B2 | 6/2016 | Kajiwara et al. |
| 9,380,287 B2 | 6/2016 | Nistico |
| 9,387,008 B2 | 7/2016 | Sarvestani |
| 9,392,129 B2 | 7/2016 | Simmons |
| 9,395,542 B2 | 7/2016 | Tilleman et al. |
| 9,398,936 B2 | 7/2016 | Razzaque et al. |
| 9,400,384 B2 | 7/2016 | Griffith |
| 9,414,041 B2 | 8/2016 | Ko |
| 9,424,611 B2 | 8/2016 | Kanjirathinkal et al. |
| 9,424,641 B2 | 8/2016 | Wiemker et al. |
| 9,427,286 B2 | 8/2016 | Siewerdsen et al. |
| 9,438,894 B2 | 9/2016 | Park |
| 9,443,488 B2 | 9/2016 | Borenstein |
| 9,453,804 B2 | 9/2016 | Tahtali |
| 9,456,878 B2 | 10/2016 | Macfarlane et al. |
| 9,465,235 B2 | 10/2016 | Chang |
| 9,468,373 B2 | 10/2016 | Larsen |
| 9,470,908 B1 | 10/2016 | Frankel |
| 9,473,766 B2 | 10/2016 | Douglas |
| 9,492,222 B2 | 11/2016 | Singh |
| 9,495,585 B2 | 11/2016 | Bicer et al. |
| 9,498,132 B2 | 11/2016 | Maier-Hein et al. |
| 9,498,231 B2 | 11/2016 | Haider et al. |
| 9,499,999 B2 | 11/2016 | Zhou |
| 9,507,155 B2 | 11/2016 | Morimoto |
| 9,513,495 B2 | 12/2016 | Waters |
| 9,521,966 B2 | 12/2016 | Schwartz |
| 9,526,443 B1 | 12/2016 | Berme |
| 9,530,382 B2 | 12/2016 | Simmons |
| 9,532,846 B2 | 1/2017 | Nakamura |
| 9,532,849 B2 | 1/2017 | Anderson et al. |
| 9,533,407 B1 * | 1/2017 | Ragner .................. B25B 13/102 |
| 9,538,962 B1 | 1/2017 | Hannaford et al. |
| 9,545,233 B2 | 1/2017 | Sirpad |
| 9,546,779 B2 | 1/2017 | Rementer |
| 9,547,174 B2 | 1/2017 | Gao et al. |
| 9,547,940 B1 | 1/2017 | Sun et al. |
| 9,557,566 B2 | 1/2017 | Fujimaki |
| 9,560,318 B2 | 1/2017 | Reina et al. |
| 9,561,095 B1 | 2/2017 | Nguyen |
| 9,565,415 B2 | 2/2017 | Zhang et al. |
| 9,572,661 B2 | 2/2017 | Robin |
| 9,576,398 B1 | 2/2017 | Zehner et al. |
| 9,576,556 B2 | 2/2017 | Simmons |
| 9,581,822 B2 | 2/2017 | Morimoto |
| 9,610,056 B2 | 4/2017 | Lavallee et al. |
| 9,612,657 B2 | 4/2017 | Bertram et al. |
| 9,626,936 B2 | 4/2017 | Bell |
| 9,629,595 B2 | 4/2017 | Walker |
| 9,633,431 B2 | 4/2017 | Merlet |
| 9,645,395 B2 | 5/2017 | Bolas et al. |
| 9,646,423 B1 | 5/2017 | Sun et al. |
| 9,672,597 B2 | 6/2017 | Amiot |
| 9,672,607 B2 | 6/2017 | Demri et al. |
| 9,672,640 B2 | 6/2017 | Kleiner |
| 9,675,306 B2 | 6/2017 | Morton |
| 9,675,319 B1 | 6/2017 | Razzaque |
| 9,684,980 B2 | 6/2017 | Royalty et al. |
| 9,690,119 B2 | 6/2017 | Garofolo et al. |
| RE46,463 E | 7/2017 | Fienbloom et al. |
| 9,693,748 B2 | 7/2017 | Rai et al. |
| 9,710,968 B2 | 7/2017 | Dillavou et al. |
| 9,713,502 B2 | 7/2017 | Finkman |
| 9,724,119 B2 | 8/2017 | Hissong |
| 9,724,165 B2 | 8/2017 | Arata et al. |
| 9,726,888 B2 | 8/2017 | Giartisio |
| 9,728,006 B2 | 8/2017 | Varga |
| 9,729,831 B2 | 8/2017 | Birnkrant |
| 9,746,739 B2 | 8/2017 | Alton et al. |
| 9,757,034 B2 | 9/2017 | Desjardins |
| 9,757,087 B2 | 9/2017 | Simon et al. |
| 9,766,441 B2 | 9/2017 | Rappel |
| 9,766,459 B2 | 9/2017 | Alton et al. |
| 9,767,608 B2 | 9/2017 | Lee et al. |
| 9,770,203 B1 | 9/2017 | Berme |
| 9,772,102 B1 | 9/2017 | Ferguson |
| 9,772,495 B2 | 9/2017 | Tam |
| 9,791,138 B1 | 10/2017 | Feinbloom |
| 9,800,995 B2 | 10/2017 | Libin |
| 9,805,504 B2 | 10/2017 | Zhang |
| 9,808,148 B2 | 11/2017 | Miller |
| 9,839,448 B2 | 12/2017 | Reckling et al. |
| 9,844,413 B2 | 12/2017 | Daon et al. |
| 9,851,080 B2 | 12/2017 | Wilt |
| 9,858,663 B2 | 1/2018 | Penney et al. |
| 9,861,446 B2 | 1/2018 | Lang |
| 9,864,214 B2 | 1/2018 | Fass |
| 9,872,733 B2 | 1/2018 | Shoham et al. |
| 9,875,544 B2 | 1/2018 | Rai et al. |
| 9,877,642 B2 | 1/2018 | Duret |
| 9,885,465 B2 | 2/2018 | Nguyen |
| 9,886,552 B2 | 2/2018 | Dillavou et al. |
| 9,886,760 B2 | 2/2018 | Liu et al. |
| 9,892,564 B1 | 2/2018 | Cvetko et al. |
| 9,898,866 B2 | 2/2018 | Fuchs et al. |
| 9,901,414 B2 | 2/2018 | Lively |
| 9,911,187 B2 | 3/2018 | Steinle |
| 9,911,236 B2 | 3/2018 | Bar et al. |
| 9,927,611 B2 | 3/2018 | Rudy |
| 9,928,629 B2 | 3/2018 | Benishti et al. |
| 9,940,750 B2 | 4/2018 | Dillavou et al. |
| 9,943,374 B2 | 4/2018 | Merritt et al. |
| 9,947,110 B2 | 4/2018 | Haimerl |
| 9,952,664 B2 | 4/2018 | Border et al. |
| 9,956,054 B2 | 5/2018 | Aguirre-Valencia |
| 9,958,674 B2 | 5/2018 | Border |
| 9,959,620 B2 | 5/2018 | Merlet |
| 9,959,629 B2 | 5/2018 | Dillavou et al. |

(56) References Cited

U.S. PATENT DOCUMENTS

| | | |
|---|---|---|
| 9,965,681 B2 | 5/2018 | Border et al. |
| 9,968,297 B2 | 5/2018 | Connor |
| 9,980,780 B2 | 5/2018 | Lang |
| 9,986,228 B2 | 5/2018 | Woods |
| D824,523 S | 7/2018 | Paoli et al. |
| 10,010,379 B1 | 7/2018 | Gibby et al. |
| 10,013,531 B2 | 7/2018 | Richards |
| 10,015,243 B2 | 7/2018 | Kazerani et al. |
| 10,016,243 B2 | 7/2018 | Esterberg |
| 10,022,064 B2 | 7/2018 | Kim et al. |
| 10,022,065 B2 | 7/2018 | Yishai et al. |
| 10,022,104 B2 | 7/2018 | Sell et al. |
| 10,023,615 B2 | 7/2018 | Bonny |
| 10,026,015 B2 | 7/2018 | Cavusoglu |
| 10,034,713 B2 | 7/2018 | Yang et al. |
| 10,042,167 B2 | 8/2018 | McDowall et al. |
| 10,046,165 B2 | 8/2018 | Frewin |
| 10,055,838 B2 | 8/2018 | Elenbaas et al. |
| 10,066,816 B2 | 9/2018 | Chang |
| 10,067,359 B1 | 9/2018 | Ushakov |
| 10,073,515 B2 | 9/2018 | Awdeh |
| 10,080,616 B2 | 9/2018 | Wilkinson et al. |
| 10,082,680 B2 | 9/2018 | Chang |
| 10,085,709 B2 | 10/2018 | Lavallee et al. |
| 10,105,187 B2 | 10/2018 | Corndorf et al. |
| 10,107,483 B2 | 10/2018 | Oren |
| 10,108,833 B2 | 10/2018 | Hong et al. |
| 10,123,840 B2 | 11/2018 | Dorman |
| 10,130,378 B2 | 11/2018 | Bryan |
| 10,132,483 B1 | 11/2018 | Feinbloom |
| 10,134,166 B2 | 11/2018 | Benishti et al. |
| 10,134,194 B2 | 11/2018 | Kepner |
| 10,139,652 B2 | 11/2018 | Windham |
| 10,139,920 B2 | 11/2018 | Isaacs |
| 10,142,496 B1 | 11/2018 | Rao |
| 10,151,928 B2 | 12/2018 | Ushakov |
| 10,154,239 B2 | 12/2018 | Casas |
| 10,159,530 B2 | 12/2018 | Lang |
| 10,163,207 B2 | 12/2018 | Merlet |
| 10,166,079 B2 | 1/2019 | McLachlin et al. |
| 10,175,507 B2 | 1/2019 | Nakamura |
| 10,175,753 B2 | 1/2019 | Boesen |
| 10,181,361 B2 | 1/2019 | Dillavou et al. |
| 10,186,055 B2 | 1/2019 | Takahashi |
| 10,188,672 B2 | 1/2019 | Wagner |
| 10,194,131 B2 | 1/2019 | Casas |
| 10,194,990 B2 | 2/2019 | Amanatullah et al. |
| 10,194,993 B2 | 2/2019 | Roger et al. |
| 10,195,076 B2 | 2/2019 | Fateh |
| 10,197,803 B2 | 2/2019 | Badiali et al. |
| 10,197,816 B2 | 2/2019 | Waisman |
| 10,207,315 B2 | 2/2019 | Appleby |
| 10,212,517 B1 | 2/2019 | Beltran et al. |
| 10,230,719 B2 | 3/2019 | Vaugn |
| 10,231,893 B2 | 3/2019 | Lei |
| 10,235,606 B2 | 3/2019 | Miao |
| 10,240,769 B1 | 3/2019 | Braganca |
| 10,247,965 B2 | 4/2019 | Ton |
| 10,251,724 B2 | 4/2019 | McLachlin et al. |
| 10,261,324 B2 | 4/2019 | Chuang et al. |
| 10,262,424 B2 | 4/2019 | Ketcha et al. |
| 10,274,731 B2 | 4/2019 | Maimone |
| 10,278,777 B1 | 5/2019 | Lang |
| 10,292,768 B2 | 5/2019 | Lang |
| 10,296,805 B2 | 5/2019 | Yang et al. |
| 10,319,154 B1 | 6/2019 | Chakravarthula et al. |
| 10,326,975 B2 | 6/2019 | Casas |
| 10,332,267 B2 | 6/2019 | Rai et al. |
| 10,339,719 B2 | 7/2019 | Jagga et al. |
| 10,352,543 B1 | 7/2019 | Braganca |
| 10,357,146 B2 | 7/2019 | Fiebel |
| 10,357,574 B2 | 7/2019 | Hilderbrand |
| 10,366,489 B2 | 7/2019 | Boettger et al. |
| 10,368,947 B2 | 8/2019 | Lang |
| 10,368,948 B2 | 8/2019 | Tripathi |
| 10,382,748 B2 | 8/2019 | Benishti et al. |
| 10,383,654 B2 | 8/2019 | Yilmaz et al. |
| 10,386,645 B2 | 8/2019 | Shousha |
| 10,388,076 B2 | 8/2019 | Bar-Zeev et al. |
| 10,398,514 B2 | 9/2019 | Ryan et al. |
| 10,401,657 B2 | 9/2019 | Jiang et al. |
| 10,405,825 B2 | 9/2019 | Rai et al. |
| 10,405,927 B1 | 9/2019 | Lang |
| 10,413,752 B2 | 9/2019 | Berlinger et al. |
| 10,419,655 B2 | 9/2019 | Sivan |
| 10,420,626 B2 | 9/2019 | Tokuda et al. |
| 10,420,813 B2 | 9/2019 | Newell-Rogers |
| 10,424,115 B2 | 9/2019 | Ellerbrock |
| D862,469 S | 10/2019 | Sadot et al. |
| 10,426,554 B2 | 10/2019 | Siewerdsen et al. |
| 10,429,675 B2 | 10/2019 | Greget |
| 10,431,008 B2 | 10/2019 | Djajadiningrat |
| 10,433,814 B2 | 10/2019 | Razzaque |
| 10,434,335 B2 | 10/2019 | Takahashi |
| 10,441,236 B2 | 10/2019 | Bar-Tal et al. |
| 10,444,514 B2 | 10/2019 | Abou Shousha et al. |
| 10,447,947 B2 | 10/2019 | Liu |
| 10,448,003 B2 | 10/2019 | Grafenberg |
| 10,449,040 B2 | 10/2019 | Lashinski |
| 10,453,187 B2 | 10/2019 | Peterson |
| 10,463,434 B2 | 11/2019 | Siegler et al. |
| 10,465,892 B1 | 11/2019 | Feinbloom |
| 10,466,487 B2 | 11/2019 | Blum et al. |
| 10,470,732 B2 | 11/2019 | Baumgart |
| 10,473,314 B1 | 11/2019 | Braganca |
| 10,485,989 B2 | 11/2019 | Jordan |
| 10,488,663 B2 | 11/2019 | Choi |
| D869,772 S | 12/2019 | Gand |
| D870,977 S | 12/2019 | Berggren et al. |
| 10,492,755 B2 | 12/2019 | Lin et al. |
| 10,499,997 B2 | 12/2019 | Weinstein et al. |
| 10,502,363 B2 | 12/2019 | Edwards et al. |
| 10,504,231 B2 | 12/2019 | Fiala |
| 10,507,066 B2 | 12/2019 | DiMaio |
| 10,511,822 B2 | 12/2019 | Casas |
| 10,517,544 B2 | 12/2019 | Taguchi |
| 10,537,395 B2 | 1/2020 | Perez |
| 10,540,780 B1 | 1/2020 | Cousins |
| 10,543,485 B2 | 1/2020 | Ismagilov |
| 10,546,423 B2 | 1/2020 | Jones et al. |
| 10,548,557 B2 | 2/2020 | Lim |
| 10,555,775 B2 | 2/2020 | Hoffman |
| 10,568,535 B2 | 2/2020 | Roberts et al. |
| 10,571,696 B2 | 2/2020 | Urey et al. |
| 10,571,716 B2 | 2/2020 | Chapiro |
| 10,573,086 B2 | 2/2020 | Bar-Zeev et al. |
| 10,573,087 B2 | 2/2020 | Gallop et al. |
| 10,602,114 B2 | 2/2020 | Casas |
| 10,577,630 B2 | 3/2020 | Zhang |
| 10,586,400 B2 | 3/2020 | Douglas |
| 10,591,737 B2 | 3/2020 | Yildiz et al. |
| 10,592,748 B1 | 3/2020 | Cousins |
| 10,595,716 B2 | 3/2020 | Nazareth |
| 10,601,950 B2 | 3/2020 | Devam et al. |
| 10,603,113 B2 | 3/2020 | Lang |
| 10,603,133 B2 | 3/2020 | Wang et al. |
| 10,606,085 B2 | 3/2020 | Toyama |
| 10,594,998 B1 | 4/2020 | Casas |
| 10,610,172 B2 | 4/2020 | Hummel et al. |
| 10,610,179 B2 | 4/2020 | Altmann |
| 10,613,352 B2 | 4/2020 | Knoll |
| 10,617,566 B2 | 4/2020 | Esmonde |
| 10,620,460 B2 | 4/2020 | Carabin |
| 10,621,738 B2 | 4/2020 | Miao et al. |
| 10,625,099 B2 | 4/2020 | Takahashi |
| 10,626,473 B2 | 4/2020 | Mariani |
| 10,631,905 B2 | 4/2020 | Asfora et al. |
| 10,631,907 B2 | 4/2020 | Zucker |
| 10,634,331 B1 | 4/2020 | Feinbloom |
| 10,634,921 B2 | 4/2020 | Blum et al. |
| 10,638,080 B2 | 4/2020 | Ovchinnikov |
| 10,646,285 B2 | 5/2020 | Siemionow et al. |
| 10,650,513 B2 | 5/2020 | Penney et al. |
| 10,650,594 B2 | 5/2020 | Jones |

(56) References Cited

U.S. PATENT DOCUMENTS

| | | |
|---|---|---|
| 10,652,525 B2 | 5/2020 | Woods |
| 10,653,495 B2 | 5/2020 | Gregerson et al. |
| 10,660,715 B2 | 5/2020 | Dozeman |
| 10,663,738 B2 | 5/2020 | Carlvik |
| 10,665,033 B2 | 5/2020 | Bar-Zeev et al. |
| 10,670,937 B2 | 6/2020 | Alton et al. |
| 10,672,145 B2 | 6/2020 | Albiol et al. |
| 10,682,112 B2 | 6/2020 | Pizaine |
| 10,682,767 B2 | 6/2020 | Grafenberg et al. |
| 10,687,901 B2 | 6/2020 | Thomas |
| 10,691,397 B1 | 6/2020 | Clements |
| 10,702,713 B2 | 7/2020 | Mori |
| 10,706,540 B2 | 7/2020 | Merlet |
| 10,709,398 B2 | 7/2020 | Schweizer |
| 10,713,801 B2 | 7/2020 | Jordan |
| 10,716,643 B2 | 7/2020 | Justin et al. |
| 10,722,733 B2 | 7/2020 | Takahashi |
| 10,725,535 B2 | 7/2020 | Yu |
| 10,731,832 B2 | 8/2020 | Koo |
| 10,732,721 B1 | 8/2020 | Clements |
| 10,742,949 B2 | 8/2020 | Casas |
| 10,743,939 B1 | 8/2020 | Lang |
| 10,743,943 B2 | 8/2020 | Razeto et al. |
| 10,747,315 B2 | 8/2020 | Tungare |
| 10,748,319 B1 | 8/2020 | Tao et al. |
| 10,758,315 B2 | 9/2020 | Johnson et al. |
| 10,777,094 B1 | 9/2020 | Rao |
| 10,777,315 B2 | 9/2020 | Zehavi |
| 10,781,482 B2 | 9/2020 | Gubatayao |
| 10,792,110 B2 | 10/2020 | Leung et al. |
| 10,799,145 B2 | 10/2020 | West et al. |
| 10,799,296 B2 | 10/2020 | Lang |
| 10,799,298 B2 | 10/2020 | Crawford et al. |
| 10,799,316 B2 | 10/2020 | Sela et al. |
| 10,810,799 B2 | 10/2020 | Tepper et al. |
| 10,818,019 B2 | 10/2020 | Piat |
| 10,818,101 B2 | 10/2020 | Gallop et al. |
| 10,818,199 B2 | 10/2020 | Buras et al. |
| 10,825,563 B2 | 11/2020 | Gibby et al. |
| 10,827,164 B2 | 11/2020 | Perreault et al. |
| 10,831,943 B2 | 11/2020 | Santarone |
| 10,835,296 B2 | 11/2020 | Elimelech |
| 10,838,206 B2 | 11/2020 | Fortin-Deschenes et al. |
| 10,839,629 B2 | 11/2020 | Jones |
| 10,839,956 B2 | 11/2020 | Beydoun et al. |
| 10,841,556 B2 | 11/2020 | Casas |
| 10,842,002 B2 | 11/2020 | Chang |
| 10,842,461 B2 | 11/2020 | Johnson et al. |
| 10,849,691 B2 | 12/2020 | Zucker |
| 10,849,693 B2 | 12/2020 | Lang |
| 10,849,710 B2 | 12/2020 | Liu |
| 10,861,236 B2 | 12/2020 | Geri et al. |
| 10,865,220 B2 | 12/2020 | Ebetino |
| 10,869,517 B1 | 12/2020 | Halpern |
| 10,869,727 B2 | 12/2020 | Yanof et al. |
| 10,872,472 B2 | 12/2020 | Watola |
| 10,877,262 B1 | 12/2020 | Luxembourg |
| 10,877,296 B2 | 12/2020 | Lindsey |
| 10,878,639 B2 | 12/2020 | Douglas et al. |
| 10,893,260 B2 | 1/2021 | Trail et al. |
| 10,895,742 B2 | 1/2021 | Schneider |
| 10,895,743 B2 | 1/2021 | Dausmann |
| 10,895,906 B2 | 1/2021 | West et al. |
| 10,898,151 B2 | 1/2021 | Harding et al. |
| 10,908,420 B2 | 2/2021 | Lee et al. |
| 10,921,595 B2 | 2/2021 | Rakshit |
| 10,921,613 B2 | 2/2021 | Gupta et al. |
| 10,928,321 B2 | 2/2021 | Rawle |
| 10,928,638 B2 | 2/2021 | Ninan |
| 10,929,670 B1 | 2/2021 | Troy et al. |
| 10,935,815 B1 | 3/2021 | Castaneda |
| 10,935,816 B2 | 3/2021 | Ban |
| 10,936,537 B2 | 3/2021 | Huston |
| 10,939,973 B2 | 3/2021 | DiMaio |
| 10,939,977 B2 | 3/2021 | Messinger et al. |
| 10,941,933 B2 | 3/2021 | Ferguson |
| 10,946,108 B2 | 3/2021 | Zhang |
| 10,950,338 B2 | 3/2021 | Douglas |
| 10,951,872 B2 | 3/2021 | Casas |
| 10,964,095 B1 | 3/2021 | Douglas |
| 10,964,124 B1 | 3/2021 | Douglas |
| 10,966,768 B2 | 4/2021 | Poulos |
| 10,969,587 B2 | 4/2021 | McDowall et al. |
| 10,993,754 B2 | 5/2021 | Kuntz et al. |
| 11,000,335 B2 | 5/2021 | Dorman |
| 11,002,994 B2 | 5/2021 | Jiang et al. |
| 11,006,093 B1 | 5/2021 | Hegyi |
| 11,013,550 B2 | 5/2021 | Rioux et al. |
| 11,013,560 B2 | 5/2021 | Lang |
| 11,013,562 B2 | 5/2021 | Marti |
| 11,013,573 B2 | 5/2021 | Chang |
| 11,013,900 B2 | 5/2021 | Malek |
| 11,016,302 B2 | 5/2021 | Freeman et al. |
| 11,019,988 B2 | 6/2021 | Fiebel |
| 11,027,027 B2 | 6/2021 | Manning |
| 11,029,147 B2 | 6/2021 | Abovitz et al. |
| 11,030,809 B2 | 6/2021 | Wang |
| 11,041,173 B2 | 6/2021 | Zhang |
| 11,045,663 B2 | 6/2021 | Mori |
| 11,049,293 B2 | 6/2021 | Chae |
| 11,049,476 B2 | 6/2021 | Fuchs et al. |
| 11,050,990 B2 | 6/2021 | Casas |
| 11,057,505 B2 | 7/2021 | Dharmatilleke |
| 11,058,390 B1 | 7/2021 | Douglas |
| 11,061,257 B1 | 7/2021 | Hakim |
| 11,064,904 B2 | 7/2021 | Kay et al. |
| 11,065,062 B2 | 7/2021 | Frushour |
| 11,067,387 B2 | 7/2021 | Marell |
| 11,071,497 B2 | 7/2021 | Hallack |
| 11,079,596 B2 | 8/2021 | Hua et al. |
| 11,087,039 B2 | 8/2021 | Duff |
| 11,090,019 B2 | 8/2021 | Siemionow et al. |
| 11,097,129 B2 | 8/2021 | Sakata |
| 11,099,376 B1 | 8/2021 | Steier |
| 11,103,320 B2 | 8/2021 | LeBoeuf |
| D930,162 S | 9/2021 | Cremer et al. |
| 11,109,762 B1 | 9/2021 | Steier |
| 11,112,611 B1 | 9/2021 | Kessler et al. |
| 11,122,164 B2 | 9/2021 | Gigante |
| 11,123,604 B2 | 9/2021 | Fung |
| 11,129,562 B2 | 9/2021 | Roberts et al. |
| 11,132,055 B2 | 9/2021 | Jones et al. |
| 11,135,015 B2 | 10/2021 | Crawford |
| 11,135,016 B2 | 10/2021 | Frielinghaus et al. |
| 11,137,610 B1 | 10/2021 | Kessler et al. |
| 11,141,221 B2 | 10/2021 | Hobeika |
| 11,153,549 B2 | 10/2021 | Casas |
| 11,153,555 B1 | 11/2021 | Healy et al. |
| 11,163,176 B2 | 11/2021 | Karafin |
| 11,164,324 B2 | 11/2021 | Liu |
| 11,166,006 B2 | 11/2021 | Hegyi |
| 11,169,380 B2 | 11/2021 | Manly et al. |
| 11,172,990 B2 | 11/2021 | Lang |
| 11,179,136 B2 | 11/2021 | Kohli |
| 11,180,557 B2 | 11/2021 | Noelle |
| 11,181,747 B1 | 11/2021 | Kessler et al. |
| 11,185,891 B2 | 11/2021 | Cousins |
| 11,187,907 B2 | 11/2021 | Osterman et al. |
| 11,202,682 B2 | 12/2021 | Staunton |
| 11,207,150 B2 | 12/2021 | Healy |
| 11,217,028 B2 | 1/2022 | Jones |
| 11,224,483 B2 | 1/2022 | Steinberg et al. |
| 11,224,763 B2 | 1/2022 | Takahashi |
| 11,227,417 B2 | 1/2022 | Berlinger |
| 11,231,787 B2 | 1/2022 | Isaacs et al. |
| 11,243,404 B2 | 2/2022 | McDowall et al. |
| 11,244,508 B2 | 2/2022 | Kazanzides et al. |
| 11,253,216 B2 | 2/2022 | Crawford et al. |
| 11,253,323 B2 | 2/2022 | Hughes et al. |
| 11,257,190 B2 | 2/2022 | Mao |
| 11,257,241 B2 | 2/2022 | Tao |
| 11,263,772 B2 | 3/2022 | Siemionow et al. |
| 11,269,401 B2 | 3/2022 | West et al. |
| 11,272,151 B2 | 3/2022 | Casas |

(56) References Cited

U.S. PATENT DOCUMENTS

| | | |
|---|---|---|
| 11,278,359 B2 | 3/2022 | Siemionow et al. |
| 11,278,413 B1 | 3/2022 | Lang |
| 11,280,480 B2 | 3/2022 | Wilt |
| 11,284,846 B2 | 3/2022 | Graumann |
| 11,311,341 B2 | 3/2022 | Lang |
| 11,291,521 B2 | 4/2022 | Im |
| 11,294,167 B2 | 4/2022 | Ishimoda |
| 11,297,285 B2 | 4/2022 | Pierce |
| 11,300,252 B2 | 4/2022 | Nguyen |
| 11,300,790 B2 | 4/2022 | Cheng et al. |
| 11,304,621 B2 | 4/2022 | Merschon et al. |
| 11,304,759 B2 | 4/2022 | Kovtun et al. |
| 11,307,402 B2 | 4/2022 | Steier |
| 11,308,663 B2 | 4/2022 | Alhrishy et al. |
| 11,317,973 B2 | 5/2022 | Calloway |
| 11,337,763 B2 | 5/2022 | Choi |
| 11,348,257 B2 | 5/2022 | Lang |
| 11,350,072 B1 | 5/2022 | Casas |
| 11,350,965 B2 | 6/2022 | Yilmaz et al. |
| 11,351,006 B2 | 6/2022 | Aferzon |
| 11,354,813 B2 | 6/2022 | Piat et al. |
| 11,360,315 B2 | 6/2022 | Tu |
| 11,373,342 B2 | 6/2022 | Stafford et al. |
| 11,382,699 B2 | 7/2022 | Wassall |
| 11,382,700 B2 | 7/2022 | Calloway |
| 11,382,712 B2 * | 7/2022 | Elimelech ............... G06T 11/00 |
| 11,382,713 B2 | 7/2022 | Healy |
| 11,389,252 B2 | 7/2022 | Gera et al. |
| 11,393,229 B2 | 7/2022 | Zhou et al. |
| 11,399,895 B2 | 8/2022 | Soper et al. |
| 11,402,524 B2 | 8/2022 | Song et al. |
| 11,406,338 B2 | 8/2022 | Tolkowsky |
| 11,412,202 B2 | 8/2022 | Hegyi |
| 11,423,554 B2 | 8/2022 | Borsdorf et al. |
| 11,430,203 B2 | 8/2022 | Navab et al. |
| 11,432,828 B1 | 9/2022 | Lang |
| 11,432,931 B2 | 9/2022 | Lang |
| 11,443,428 B2 | 9/2022 | Petersen et al. |
| 11,443,431 B2 | 9/2022 | Flossmann et al. |
| 11,452,568 B2 | 9/2022 | Lang |
| 11,452,570 B2 | 9/2022 | Tolkowsky |
| 11,460,915 B2 | 10/2022 | Frielinghaus |
| 11,461,936 B2 | 10/2022 | Freeman et al. |
| 11,461,983 B2 | 10/2022 | Jones |
| 11,464,580 B2 | 10/2022 | Kemp et al. |
| 11,464,581 B2 | 10/2022 | Calloway |
| 11,475,625 B1 | 10/2022 | Douglas |
| 11,478,214 B2 | 10/2022 | Siewerdsen et al. |
| 11,483,532 B2 | 10/2022 | Casas |
| 11,488,021 B2 | 11/2022 | Sun et al. |
| 11,490,986 B2 | 11/2022 | Ben-Yishai |
| 11,510,750 B2 | 11/2022 | Dulin et al. |
| 11,513,358 B2 | 11/2022 | McDowall et al. |
| 11,527,002 B2 | 12/2022 | Govari |
| 11,528,393 B2 | 12/2022 | Garofolo et al. |
| 11,544,031 B2 | 1/2023 | Harviainen |
| 11,573,420 B2 | 2/2023 | Sarma et al. |
| 11,589,927 B2 | 2/2023 | Oezbek et al. |
| 11,627,924 B2 | 4/2023 | Alexandroni et al. |
| 11,644,675 B2 | 5/2023 | Manly et al. |
| 11,648,016 B2 | 5/2023 | Hathaway et al. |
| 11,651,499 B2 | 5/2023 | Wang et al. |
| 11,657,518 B2 | 5/2023 | Ketcha et al. |
| 11,666,458 B2 | 6/2023 | Kim et al. |
| 11,669,984 B2 | 6/2023 | Siewerdsen et al. |
| 11,686,947 B2 | 6/2023 | Loyola et al. |
| 11,699,236 B2 | 7/2023 | Avital et al. |
| 11,712,582 B2 | 8/2023 | Miyazaki et al. |
| 11,715,210 B2 | 8/2023 | Haslam et al. |
| 11,719,941 B2 | 8/2023 | Russell |
| 11,730,389 B2 | 8/2023 | Farshad et al. |
| 11,733,516 B2 | 8/2023 | Edwin et al. |
| 11,734,901 B2 | 8/2023 | Jones et al. |
| 11,744,657 B2 | 9/2023 | Leboeuf et al. |
| 11,750,794 B2 | 9/2023 | Benishti et al. |
| 11,766,296 B2 | 9/2023 | Wolf et al. |
| 11,798,178 B2 | 10/2023 | Merlet |
| 11,801,097 B2 | 10/2023 | Crawford et al. |
| 11,801,115 B2 | 10/2023 | Elimelech et al. |
| 11,808,943 B2 | 11/2023 | Robaina et al. |
| 11,815,683 B2 | 11/2023 | Sears et al. |
| 11,826,111 B2 | 11/2023 | Mahfouz |
| 11,832,886 B2 | 12/2023 | Dorman |
| 11,838,493 B2 | 12/2023 | Healy et al. |
| 11,839,433 B2 | 12/2023 | Schaewe et al. |
| 11,839,501 B2 | 12/2023 | Takahashi et al. |
| 11,864,934 B2 | 1/2024 | Junio et al. |
| 11,885,752 B2 | 1/2024 | St-Aubin et al. |
| 11,892,647 B2 | 2/2024 | Hung et al. |
| 11,896,445 B2 | 2/2024 | Gera et al. |
| 11,900,620 B2 | 2/2024 | Lalys et al. |
| 11,914,155 B2 | 2/2024 | Zhu et al. |
| 11,918,310 B1 | 3/2024 | Roh et al. |
| 11,922,631 B2 | 3/2024 | Haslam et al. |
| 11,941,814 B2 | 3/2024 | Crawford et al. |
| 11,944,508 B1 | 4/2024 | Cowin et al. |
| 11,948,265 B2 | 4/2024 | Gibby et al. |
| 11,950,968 B2 | 4/2024 | Wiggermann |
| 11,957,420 B2 | 4/2024 | Lang |
| 11,961,193 B2 | 4/2024 | Pelzl et al. |
| 11,963,723 B2 | 4/2024 | Vilsmeier et al. |
| 11,972,582 B2 | 4/2024 | Yan et al. |
| 11,974,819 B2 | 5/2024 | Finley et al. |
| 11,974,887 B2 | 5/2024 | Elimelech et al. |
| 11,977,232 B2 | 5/2024 | Wu et al. |
| 11,980,429 B2 | 5/2024 | Wolf et al. |
| 11,980,506 B2 | 5/2024 | Wolf et al. |
| 11,980,507 B2 | 5/2024 | Elimelech et al. |
| 11,980,508 B2 | 5/2024 | Elimelech et al. |
| 11,983,824 B2 | 5/2024 | Avisar et al. |
| 12,002,171 B2 | 6/2024 | Jones et al. |
| 12,010,285 B2 | 6/2024 | Quiles Casas |
| 12,014,497 B2 | 6/2024 | Hong et al. |
| 12,019,314 B1 | 6/2024 | Steines et al. |
| 12,044,856 B2 | 7/2024 | Gera et al. |
| 12,044,858 B2 | 7/2024 | Gera et al. |
| 12,063,345 B2 | 8/2024 | Benishti et al. |
| 12,069,233 B2 | 8/2024 | Benishti et al. |
| 12,076,196 B2 | 9/2024 | Elimelech et al. |
| 2002/0082498 A1 | 6/2002 | Wendt et al. |
| 2003/0059097 A1 | 3/2003 | Abovitz et al. |
| 2003/0117393 A1 | 6/2003 | Sauer et al. |
| 2003/0130576 A1 | 7/2003 | Seeley |
| 2003/0156144 A1 | 8/2003 | Morita |
| 2003/0210812 A1 | 11/2003 | Khamene et al. |
| 2003/0225329 A1 * | 12/2003 | Rossner ............... A61B 90/39 606/130 |
| 2004/0019263 A1 | 1/2004 | Jutras et al. |
| 2004/0030237 A1 | 2/2004 | Lee et al. |
| 2004/0138556 A1 | 7/2004 | Cosman |
| 2004/0152955 A1 | 8/2004 | McGinley et al. |
| 2004/0171930 A1 * | 9/2004 | Grimm ............... A61B 90/39 606/80 |
| 2005/0017972 A1 | 1/2005 | Poole et al. |
| 2005/0024586 A1 | 2/2005 | Teiwes et al. |
| 2005/0119639 A1 | 6/2005 | McCombs et al. |
| 2005/0154296 A1 * | 7/2005 | Lechner ......... A61B 17/00234 600/429 |
| 2005/0203367 A1 | 9/2005 | Ahmed et al. |
| 2005/0203380 A1 | 9/2005 | Sauer et al. |
| 2005/0215879 A1 | 9/2005 | Chuanggui |
| 2005/0267358 A1 | 12/2005 | Tuma et al. |
| 2006/0072124 A1 | 4/2006 | Smetak et al. |
| 2006/0134198 A1 | 6/2006 | Tawa |
| 2006/0147100 A1 | 7/2006 | Fitzpatrick |
| 2006/0176242 A1 | 8/2006 | Jaramaz et al. |
| 2007/0018975 A1 | 1/2007 | Chuanggui et al. |
| 2007/0058261 A1 | 3/2007 | Sugihara et al. |
| 2007/0100325 A1 | 5/2007 | Jutras et al. |
| 2007/0233371 A1 | 10/2007 | Stoschek et al. |
| 2008/0007645 A1 | 1/2008 | McCutchen |
| 2008/0035266 A1 | 2/2008 | Danziger |
| 2008/0085033 A1 | 4/2008 | Haven et al. |
| 2008/0159612 A1 | 7/2008 | Fu |

(56) References Cited

U.S. PATENT DOCUMENTS

| | | |
|---|---|---|
| 2008/0183065 A1 | 7/2008 | Goldbach |
| 2008/0221625 A1 | 9/2008 | Hufner et al. |
| 2008/0253527 A1 | 10/2008 | Boyden et al. |
| 2008/0262812 A1 | 10/2008 | Arata et al. |
| 2008/0287728 A1 | 11/2008 | Mostafavi et al. |
| 2009/0005961 A1 | 1/2009 | Grabowski et al. |
| 2009/0018437 A1 | 1/2009 | Cooke |
| 2009/0024127 A1 | 1/2009 | Lechner et al. |
| 2009/0062869 A1 | 3/2009 | Claverie et al. |
| 2009/0099445 A1 | 4/2009 | Burger |
| 2009/0036902 A1 | 5/2009 | Dimaio et al. |
| 2009/0227847 A1 | 9/2009 | Tepper et al. |
| 2009/0285366 A1 | 11/2009 | Essenreiter et al. |
| 2009/0300540 A1 | 12/2009 | Russell |
| 2010/0076305 A1 | 3/2010 | Maier-Hein et al. |
| 2010/0094308 A1 | 4/2010 | Tatsumi et al. |
| 2010/0106010 A1 | 4/2010 | Rubner et al. |
| 2010/0114110 A1* | 5/2010 | Taft .................. A61B 17/3421 600/114 |
| 2010/0149073 A1 | 6/2010 | Chaum et al. |
| 2010/0172567 A1 | 7/2010 | Prokoski |
| 2010/0210939 A1 | 8/2010 | Hartmann et al. |
| 2010/0266220 A1 | 10/2010 | Zagorchev et al. |
| 2010/0274124 A1 | 10/2010 | Jascob et al. |
| 2011/0004259 A1 | 1/2011 | Stallings et al. |
| 2011/0098553 A1 | 4/2011 | Robbins et al. |
| 2011/0105895 A1 | 5/2011 | Kornblau et al. |
| 2011/0216060 A1 | 9/2011 | Weising et al. |
| 2011/0245625 A1 | 10/2011 | Trovato et al. |
| 2011/0254922 A1 | 10/2011 | Schaerer et al. |
| 2011/0306873 A1 | 12/2011 | Shenai et al. |
| 2012/0014608 A1 | 1/2012 | Watanabe et al. |
| 2012/0068913 A1 | 3/2012 | Bar-Zeev et al. |
| 2012/0078236 A1 | 3/2012 | Schoepp |
| 2012/0109151 A1 | 5/2012 | Maier-Hein et al. |
| 2012/0143050 A1 | 6/2012 | Heigl |
| 2012/0155064 A1 | 6/2012 | Waters |
| 2012/0162452 A1 | 6/2012 | Liu |
| 2012/0182605 A1 | 7/2012 | Hall et al. |
| 2012/0201421 A1 | 8/2012 | Hartmann et al. |
| 2012/0216411 A1 | 8/2012 | Wevers et al. |
| 2012/0224260 A1 | 9/2012 | Healy et al. |
| 2012/0289777 A1 | 11/2012 | Chopra et al. |
| 2012/0306850 A1 | 12/2012 | Balan et al. |
| 2012/0320100 A1 | 12/2012 | Machida et al. |
| 2013/0002928 A1 | 1/2013 | Imai |
| 2013/0009853 A1 | 1/2013 | Hesselink et al. |
| 2013/0038632 A1 | 2/2013 | Dillavou et al. |
| 2013/0050258 A1 | 2/2013 | Liu et al. |
| 2013/0050833 A1 | 2/2013 | Lewis et al. |
| 2013/0057581 A1 | 3/2013 | Meier |
| 2013/0079829 A1 | 3/2013 | Globerman et al. |
| 2013/0083009 A1 | 4/2013 | Geisner et al. |
| 2013/0106833 A1 | 5/2013 | Fun |
| 2013/0135734 A1 | 5/2013 | Shafer et al. |
| 2013/0135738 A1 | 5/2013 | Shafer et al. |
| 2013/0190602 A1 | 7/2013 | Liao |
| 2013/0195338 A1 | 8/2013 | Xu et al. |
| 2013/0209953 A1 | 8/2013 | Arlinsky et al. |
| 2013/0212453 A1 | 8/2013 | Gudai et al. |
| 2013/0234914 A1 | 9/2013 | Fujimaki |
| 2013/0234935 A1 | 9/2013 | Griffith |
| 2013/0237811 A1 | 9/2013 | Mihailescu et al. |
| 2013/0245461 A1 | 9/2013 | Maier-Hein et al. |
| 2013/0249787 A1 | 9/2013 | Morimota |
| 2013/0249945 A1 | 9/2013 | Kobayashi |
| 2013/0265623 A1 | 10/2013 | Sugiyama et al. |
| 2013/0267838 A1 | 10/2013 | Fronk et al. |
| 2013/0278631 A1 | 10/2013 | Border et al. |
| 2013/0278635 A1 | 10/2013 | Maggiore |
| 2013/0300760 A1 | 11/2013 | Sugano et al. |
| 2013/0342571 A1 | 12/2013 | Kinnebrew et al. |
| 2014/0031668 A1 | 1/2014 | Mobasser et al. |
| 2014/0049629 A1 | 2/2014 | Siewerdsen et al. |
| 2014/0088402 A1 | 3/2014 | Ku |
| 2014/0088990 A1 | 3/2014 | Nawana et al. |
| 2014/0104505 A1 | 4/2014 | Koenig |
| 2014/0114173 A1 | 4/2014 | Bar-Tal et al. |
| 2014/0142426 A1 | 5/2014 | Razzaque et al. |
| 2014/0168261 A1 | 6/2014 | Margolis et al. |
| 2014/0176661 A1 | 6/2014 | Smurro et al. |
| 2014/0177023 A1 | 6/2014 | Gao et al. |
| 2014/0189508 A1 | 7/2014 | Granchi et al. |
| 2014/0198129 A1 | 7/2014 | Liu et al. |
| 2014/0218291 A1 | 8/2014 | Kirk |
| 2014/0240484 A1 | 8/2014 | Kodama et al. |
| 2014/0243614 A1 | 8/2014 | Rothberg et al. |
| 2014/0256429 A1 | 9/2014 | Kobayashi et al. |
| 2014/0266983 A1 | 9/2014 | Christensen |
| 2014/0268356 A1 | 9/2014 | Bolas et al. |
| 2014/0270505 A1 | 9/2014 | McCarthy |
| 2014/0275760 A1 | 9/2014 | Lee et al. |
| 2014/0285404 A1 | 9/2014 | Takano et al. |
| 2014/0285429 A1 | 9/2014 | Simmons |
| 2014/0300632 A1 | 10/2014 | Laor |
| 2014/0300967 A1 | 10/2014 | Tilleman et al. |
| 2014/0301624 A1 | 10/2014 | Barckow et al. |
| 2014/0303491 A1 | 10/2014 | Shekhar et al. |
| 2014/0320399 A1 | 10/2014 | Kim et al. |
| 2014/0333899 A1 | 11/2014 | Smithwick |
| 2014/0336461 A1 | 11/2014 | Reiter et al. |
| 2014/0340286 A1 | 11/2014 | Machida et al. |
| 2014/0361956 A1 | 12/2014 | Mikhailov et al. |
| 2014/0371728 A1* | 12/2014 | Vaughn ................ B23B 31/22 606/1 |
| 2015/0005772 A1 | 1/2015 | Anglin et al. |
| 2015/0018672 A1 | 1/2015 | Blumhofer et al. |
| 2015/0031985 A1 | 1/2015 | Reddy et al. |
| 2015/0043798 A1 | 2/2015 | Carrell et al. |
| 2015/0070347 A1 | 3/2015 | Hofmann et al. |
| 2015/0084990 A1 | 3/2015 | Labor |
| 2015/0150641 A1 | 6/2015 | Daon et al. |
| 2015/0182293 A1* | 7/2015 | Yang .................. A61B 17/1703 600/424 |
| 2015/0209119 A1 | 7/2015 | Theodore et al. |
| 2015/0261922 A1 | 9/2015 | Nawana et al. |
| 2015/0277123 A1 | 10/2015 | Chaum et al. |
| 2015/0282735 A1 | 10/2015 | Rossner |
| 2015/0287188 A1 | 10/2015 | Gazit et al. |
| 2015/0287236 A1 | 10/2015 | Winn |
| 2015/0297314 A1 | 10/2015 | Fowler et al. |
| 2015/0305828 A1 | 10/2015 | Park et al. |
| 2015/0310668 A1 | 10/2015 | Ellerbrock |
| 2015/0338652 A1 | 11/2015 | Lim et al. |
| 2015/0338653 A1 | 11/2015 | Subramaniam et al. |
| 2015/0350517 A1 | 12/2015 | Duret et al. |
| 2015/0351863 A1 | 12/2015 | Plassky et al. |
| 2015/0363978 A1 | 12/2015 | Maimone et al. |
| 2015/0366620 A1 | 12/2015 | Cameron et al. |
| 2016/0015878 A1* | 1/2016 | Graham ............. A61M 60/419 600/16 |
| 2016/0022287 A1 | 1/2016 | Nehls |
| 2016/0030131 A1 | 2/2016 | Yang et al. |
| 2016/0054571 A1 | 2/2016 | Tazbaz et al. |
| 2016/0086380 A1 | 3/2016 | Vayser et al. |
| 2016/0103318 A1 | 4/2016 | Du et al. |
| 2016/0125603 A1 | 5/2016 | Tanji |
| 2016/0133051 A1 | 5/2016 | Aonuma et al. |
| 2016/0143699 A1 | 5/2016 | Tanji |
| 2016/0153004 A1 | 6/2016 | Zhang |
| 2016/0163045 A1 | 6/2016 | Penney et al. |
| 2016/0175064 A1 | 6/2016 | Stenile et al. |
| 2016/0178910 A1 | 6/2016 | Gudicell et al. |
| 2016/0191887 A1 | 6/2016 | Casas |
| 2016/0223822 A1 | 8/2016 | Harrison et al. |
| 2016/0246059 A1 | 8/2016 | Halpin et al. |
| 2016/0249989 A1 | 9/2016 | Devam et al. |
| 2016/0256223 A1 | 9/2016 | Haimer et al. |
| 2016/0275684 A1 | 9/2016 | Elenbaas et al. |
| 2016/0302870 A1 | 10/2016 | Wilkinson et al. |
| 2016/0324580 A1 | 11/2016 | Esterberg |
| 2016/0324583 A1 | 11/2016 | Kheradpr et al. |
| 2016/0339337 A1 | 11/2016 | Ellsworth et al. |
| 2017/0024634 A1 | 1/2017 | Miao et al. |

(56) References Cited

U.S. PATENT DOCUMENTS

| | | |
|---|---|---|
| 2017/0027650 A1 | 2/2017 | Merck et al. |
| 2017/0031163 A1 | 2/2017 | Gao et al. |
| 2017/0031179 A1 | 2/2017 | Guillot et al. |
| 2017/0045742 A1 | 2/2017 | Greenhalgh et al. |
| 2017/0065364 A1* | 3/2017 | Schuh .................. A61B 46/00 |
| 2017/0068119 A1 | 3/2017 | Antaki |
| 2017/0076501 A1 | 3/2017 | Jagga et al. |
| 2017/0086941 A1 | 3/2017 | Marti et al. |
| 2017/0112586 A1 | 4/2017 | Dhupar |
| 2017/0014119 A1 | 6/2017 | Capote et al. |
| 2017/0164919 A1 | 6/2017 | LaVallee et al. |
| 2017/0164920 A1 | 6/2017 | Lavallee et al. |
| 2017/0178375 A1 | 6/2017 | Benishti et al. |
| 2017/0220224 A1 | 8/2017 | Kodali |
| 2017/0239015 A1 | 8/2017 | Sela et al. |
| 2017/0245944 A1 | 8/2017 | Crawford et al. |
| 2017/0251900 A1 | 9/2017 | Hansen et al. |
| 2017/0252109 A1 | 9/2017 | Yang et al. |
| 2017/0258526 A1 | 9/2017 | Lang |
| 2017/0281283 A1 | 10/2017 | Siegler et al. |
| 2017/0312032 A1 | 11/2017 | Amanatullah et al. |
| 2017/0322950 A1 | 11/2017 | Han et al. |
| 2017/0348055 A1 | 12/2017 | Salcedo et al. |
| 2017/0348061 A1 | 12/2017 | Joshi et al. |
| 2017/0366773 A1 | 12/2017 | Kiraly et al. |
| 2017/0367766 A1 | 12/2017 | Mahfouz |
| 2017/0367771 A1 | 12/2017 | Tako et al. |
| 2017/0372477 A1 | 12/2017 | Penne |
| 2018/0003981 A1 | 1/2018 | Urey |
| 2018/0018791 A1 | 1/2018 | Guoyi |
| 2018/0021597 A1 | 1/2018 | Berlinger et al. |
| 2018/0028266 A1* | 2/2018 | Barnes ............... A61B 17/1703 |
| 2018/0036884 A1 | 2/2018 | Chen et al. |
| 2018/0049622 A1 | 2/2018 | Ryan et al. |
| 2018/0055579 A1 | 3/2018 | Daon et al. |
| 2018/0078316 A1 | 3/2018 | Schaewe et al. |
| 2018/0082480 A1 | 3/2018 | White et al. |
| 2018/0092667 A1* | 4/2018 | Heigl ................. A61B 17/7047 |
| 2018/0092698 A1 | 4/2018 | Chopra et al. |
| 2018/0092699 A1 | 4/2018 | Finley |
| 2018/0116732 A1 | 5/2018 | Lin et al. |
| 2018/0116741 A1* | 5/2018 | Garcia Kilroy ........ B25J 13/085 |
| 2018/0117150 A1 | 5/2018 | O'Dwyer |
| 2018/0120106 A1 | 5/2018 | Sato |
| 2018/0133871 A1* | 5/2018 | Farmer ................ B25B 23/141 |
| 2018/0153626 A1 | 6/2018 | Yang et al. |
| 2018/0182150 A1 | 6/2018 | Benishti et al. |
| 2018/0185100 A1 | 7/2018 | Weinstein et al. |
| 2018/0185113 A1 | 7/2018 | Gregerson et al. |
| 2018/0193097 A1 | 7/2018 | McLachlin et al. |
| 2018/0200002 A1 | 7/2018 | Kostrzewski et al. |
| 2018/0247128 A1 | 8/2018 | Alvi et al. |
| 2018/0262743 A1 | 9/2018 | Casas |
| 2018/0303558 A1 | 10/2018 | Thomas |
| 2018/0311011 A1 | 11/2018 | Van Beek et al. |
| 2018/0317803 A1 | 11/2018 | Ben-Yishai et al. |
| 2018/0318035 A1 | 11/2018 | McLachlin et al. |
| 2018/0368898 A1 | 12/2018 | Divincenzo et al. |
| 2019/0000372 A1 | 1/2019 | Gullotti et al. |
| 2019/0000564 A1 | 1/2019 | Navab et al. |
| 2019/0015163 A1 | 1/2019 | Abhari et al. |
| 2019/0018235 A1 | 1/2019 | Ouderkirk et al. |
| 2019/0038362 A1 | 2/2019 | Nash et al. |
| 2019/0038365 A1 | 2/2019 | Soper |
| 2019/0043238 A1 | 2/2019 | Benishti et al. |
| 2019/0043392 A1 | 2/2019 | Abele |
| 2019/0046272 A1 | 2/2019 | Zoabi et al. |
| 2019/0046276 A1 | 2/2019 | Inglese et al. |
| 2019/0053851 A1 | 2/2019 | Siemionow et al. |
| 2019/0069971 A1 | 3/2019 | Tripathi et al. |
| 2019/0080515 A1 | 3/2019 | Geri et al. |
| 2019/0105116 A1* | 4/2019 | Johnson ............. A61B 17/7074 |
| 2019/0130792 A1 | 5/2019 | Rios |
| 2019/0142519 A1 | 5/2019 | Siemionow et al. |
| 2019/0144443 A1 | 5/2019 | Jackson |
| 2019/0175228 A1 | 6/2019 | Elimelech et al. |
| 2019/0192230 A1 | 6/2019 | Siemionow et al. |
| 2019/0201106 A1 | 7/2019 | Siemionow et al. |
| 2019/0205606 A1 | 7/2019 | Zhou et al. |
| 2019/0216537 A1 | 7/2019 | Eltorai |
| 2019/0251692 A1 | 8/2019 | Schmidt-Richberg et al. |
| 2019/0251694 A1 | 8/2019 | Han et al. |
| 2019/0254753 A1 | 8/2019 | Johnson |
| 2019/0273916 A1 | 9/2019 | Benishti et al. |
| 2019/0310481 A1 | 10/2019 | Blum et al. |
| 2019/0333480 A1 | 10/2019 | Lang |
| 2019/0369660 A1 | 12/2019 | Wen et al. |
| 2019/0369717 A1 | 12/2019 | Frielinghaus |
| 2019/0378276 A1 | 12/2019 | Flossmann et al. |
| 2019/0387351 A1 | 12/2019 | Lyren |
| 2020/0019364 A1 | 1/2020 | Pond |
| 2020/0020249 A1 | 1/2020 | Jarc et al. |
| 2020/0038112 A1 | 2/2020 | Amanatullah et al. |
| 2020/0043160 A1 | 2/2020 | Mizukura et al. |
| 2020/0078100 A1 | 3/2020 | Weinstein et al. |
| 2020/0085511 A1 | 3/2020 | Oezbek et al. |
| 2020/0088997 A1 | 3/2020 | Lee |
| 2020/0159313 A1 | 3/2020 | Gibby et al. |
| 2020/0100847 A1 | 4/2020 | Siegler et al. |
| 2020/0117025 A1 | 4/2020 | Sauer |
| 2020/0129058 A1 | 4/2020 | Li |
| 2020/0129136 A1 | 4/2020 | Harding et al. |
| 2020/0129262 A1 | 4/2020 | Verard |
| 2020/0129264 A1 | 4/2020 | Onativia et al. |
| 2020/0133029 A1 | 4/2020 | Yonezawa |
| 2020/0138518 A1 | 5/2020 | Lang |
| 2020/0138618 A1 | 5/2020 | Roszkowiak et al. |
| 2020/0143594 A1 | 5/2020 | Lal et al. |
| 2020/0146546 A1 | 5/2020 | Chene |
| 2020/0151507 A1 | 5/2020 | Siemionow et al. |
| 2020/0156259 A1 | 5/2020 | Morales |
| 2020/0163723 A1 | 5/2020 | Wolf et al. |
| 2020/0163739 A1 | 5/2020 | Messinger et al. |
| 2020/0184638 A1 | 6/2020 | Meglan |
| 2020/0186786 A1 | 6/2020 | Gibby et al. |
| 2020/0188028 A1 | 6/2020 | Feiner et al. |
| 2020/0188034 A1* | 6/2020 | Lequette ................ A61B 90/39 |
| 2020/0201082 A1 | 6/2020 | Carabin |
| 2020/0229877 A1 | 7/2020 | Siemionow et al. |
| 2020/0237256 A1 | 7/2020 | Farshad et al. |
| 2020/0237459 A1 | 7/2020 | Racheli et al. |
| 2020/0237880 A1 | 7/2020 | Kent |
| 2020/0242280 A1 | 7/2020 | Pavloff et al. |
| 2020/0246074 A1 | 8/2020 | Lang |
| 2020/0246081 A1 | 8/2020 | Johnson et al. |
| 2020/0264451 A1 | 8/2020 | Blum et al. |
| 2020/0265273 A1 | 8/2020 | Wei |
| 2020/0275988 A1 | 9/2020 | Johnson |
| 2020/0281554 A1 | 9/2020 | Trini et al. |
| 2020/0288075 A1 | 9/2020 | Bonin et al. |
| 2020/0294233 A1 | 9/2020 | Merlet |
| 2020/0297427 A1 | 9/2020 | Cameron et al. |
| 2020/0305980 A1 | 10/2020 | Lang |
| 2020/0315734 A1 | 10/2020 | El Amm |
| 2020/0321099 A1 | 10/2020 | Holladay et al. |
| 2020/0323460 A1 | 10/2020 | Busza |
| 2020/0323609 A1 | 10/2020 | Johnson et al. |
| 2020/0327721 A1 | 10/2020 | Siemionow et al. |
| 2020/0330179 A1 | 10/2020 | Ton |
| 2020/0337780 A1 | 10/2020 | Winkler |
| 2020/0341283 A1 | 10/2020 | McCracken |
| 2020/0352655 A1 | 11/2020 | Freese |
| 2020/0355927 A1 | 11/2020 | Marcellin-Dibon |
| 2020/0360091 A1 | 11/2020 | Murray et al. |
| 2020/0375666 A1 | 12/2020 | Murphy |
| 2020/0377493 A1 | 12/2020 | Heiser |
| 2020/0377956 A1 | 12/2020 | Vogelstein |
| 2020/0388075 A1 | 12/2020 | Kazanzides et al. |
| 2020/0389425 A1 | 12/2020 | Bhatia |
| 2020/0390502 A1 | 12/2020 | Holthuizen et al. |
| 2020/0390503 A1 | 12/2020 | Casas et al. |
| 2020/0402647 A1 | 12/2020 | Domracheva et al. |
| 2020/0409306 A1 | 12/2020 | Gelman et al. |
| 2020/0410687 A1 | 12/2020 | Siemionow et al. |

(56) References Cited

U.S. PATENT DOCUMENTS

| | | |
|---|---|---|
| 2020/0413031 A1 | 12/2020 | Khani |
| 2021/0004956 A1 | 1/2021 | Book et al. |
| 2021/0009339 A1 | 1/2021 | Morrison et al. |
| 2021/0015560 A1 | 1/2021 | Boddington et al. |
| 2021/0015583 A1 | 1/2021 | Avisar |
| 2021/0022599 A1 | 1/2021 | Freeman et al. |
| 2021/0022808 A1 | 1/2021 | Lang |
| 2021/0022811 A1 | 1/2021 | Mahfouz |
| 2021/0022828 A1 | 1/2021 | Elimelech et al. |
| 2021/0029804 A1 | 1/2021 | Chang |
| 2021/0030374 A1 | 2/2021 | Takahashi et al. |
| 2021/0030511 A1 | 2/2021 | Wolf et al. |
| 2021/0038339 A1 | 2/2021 | Yu |
| 2021/0049825 A1 | 2/2021 | Wheelwright et al. |
| 2021/0052348 A1 | 2/2021 | Stifter et al. |
| 2021/0056687 A1 | 2/2021 | Hibbard et al. |
| 2021/0065911 A1 | 3/2021 | Goel et al. |
| 2021/0077195 A1 | 3/2021 | Saeidi |
| 2021/0077210 A1 | 3/2021 | Itkowitz |
| 2021/0080751 A1 | 3/2021 | Lindsey |
| 2021/0090344 A1 | 3/2021 | Geri et al. |
| 2021/0093391 A1 | 4/2021 | Poltaretskyi et al. |
| 2021/0093392 A1 | 4/2021 | Poltaretskyi et al. |
| 2021/0093400 A1 | 4/2021 | Quid et al. |
| 2021/0093417 A1 | 4/2021 | Liu |
| 2021/0104055 A1 | 4/2021 | Ni et al. |
| 2021/0107923 A1 | 4/2021 | Jackson |
| 2021/0109349 A1 | 4/2021 | Schneider |
| 2021/0109373 A1 | 4/2021 | Loo |
| 2021/0110517 A1 | 4/2021 | Flohr |
| 2021/0113269 A1 | 4/2021 | Vilsmeier |
| 2021/0113293 A9 | 4/2021 | Silva et al. |
| 2021/0121238 A1 | 4/2021 | Palushi et al. |
| 2021/0137634 A1 | 5/2021 | Lang et al. |
| 2021/0141887 A1 | 5/2021 | Kim et al. |
| 2021/0150702 A1 | 5/2021 | Claessen et al. |
| 2021/0157544 A1 | 5/2021 | Denton |
| 2021/0160472 A1 | 5/2021 | Casas |
| 2021/0161614 A1 | 6/2021 | Elimelech et al. |
| 2021/0162287 A1 | 6/2021 | Xing |
| 2021/0165207 A1 | 6/2021 | Peyman |
| 2021/0169504 A1 | 6/2021 | Brown |
| 2021/0169578 A1 | 6/2021 | Calloway et al. |
| 2021/0169581 A1 | 6/2021 | Calloway et al. |
| 2021/0169605 A1 | 6/2021 | Calloway et al. |
| 2021/0186647 A1 | 6/2021 | Elimelech et al. |
| 2021/0196404 A1 | 7/2021 | Wang |
| 2021/0211640 A1 | 7/2021 | Bristol et al. |
| 2021/0223577 A1 | 7/2021 | Zheng |
| 2021/0225006 A1 | 7/2021 | Grady et al. |
| 2021/0227791 A1 | 7/2021 | De Oliveira Seixas |
| 2021/0231301 A1 | 7/2021 | Hikmet et al. |
| 2021/0235061 A1 | 7/2021 | Hegyi |
| 2021/0248822 A1 | 8/2021 | Choi |
| 2021/0278675 A1 | 9/2021 | Klug et al. |
| 2021/0282887 A1 | 9/2021 | Wiggermann |
| 2021/0290046 A1 | 9/2021 | Nazareth |
| 2021/0290336 A1 | 9/2021 | Wang |
| 2021/0290394 A1 | 9/2021 | Mahfouz |
| 2021/0295108 A1 | 9/2021 | Bar |
| 2021/0295512 A1 | 9/2021 | Knoplioch et al. |
| 2021/0298795 A1* | 9/2021 | Bowling ............... B25J 9/1689 |
| 2021/0298835 A1 | 9/2021 | Wang |
| 2021/0306599 A1 | 9/2021 | Pierce |
| 2021/0311322 A1 | 10/2021 | Belanger |
| 2021/0314502 A1 | 10/2021 | Liu |
| 2021/0315636 A1 | 10/2021 | Akbarian |
| 2021/0315662 A1 | 10/2021 | Freeman et al. |
| 2021/0325684 A1 | 10/2021 | Ninan |
| 2021/0333561 A1 | 10/2021 | Oh |
| 2021/0341739 A1 | 11/2021 | Cakmakci et al. |
| 2021/0341740 A1 | 11/2021 | Cakmakci et al. |
| 2021/0346115 A1 | 11/2021 | Dulin et al. |
| 2021/0349677 A1 | 11/2021 | Baldev |
| 2021/0364802 A1 | 11/2021 | Uchiyama et al. |
| 2021/0369226 A1 | 12/2021 | Siemionow et al. |
| 2021/0371413 A1 | 12/2021 | Thurston |
| 2021/0373333 A1 | 12/2021 | Moon |
| 2021/0373344 A1 | 12/2021 | Loyola |
| 2021/0378757 A1 | 12/2021 | Bay |
| 2021/0382310 A1 | 12/2021 | Freeman et al. |
| 2021/0386482 A1 | 12/2021 | Gera et al. |
| 2021/0389590 A1 | 12/2021 | Freeman |
| 2021/0400247 A1 | 12/2021 | Casas |
| 2021/0401533 A1 | 12/2021 | Im |
| 2021/0402255 A1 | 12/2021 | Fung |
| 2021/0405369 A1 | 12/2021 | King |
| 2022/0003992 A1 | 1/2022 | Ahn |
| 2022/0007006 A1 | 1/2022 | Healy et al. |
| 2022/0008135 A1 | 1/2022 | Frielinghaus et al. |
| 2022/0038675 A1 | 2/2022 | Hegyi |
| 2022/0039873 A1 | 2/2022 | Harris |
| 2022/0051484 A1 | 2/2022 | Jones et al. |
| 2022/0054199 A1 | 2/2022 | Sivaprakasam et al. |
| 2022/0061921 A1 | 3/2022 | Crawford et al. |
| 2022/0079675 A1 | 3/2022 | Lang |
| 2022/0087746 A1 | 3/2022 | Lang |
| 2022/0113810 A1 | 4/2022 | Isaacs et al. |
| 2022/0117669 A1 | 4/2022 | Nikou et al. |
| 2022/0121041 A1 | 4/2022 | Hakim |
| 2022/0142730 A1 | 5/2022 | Wolf et al. |
| 2022/0155861 A1 | 5/2022 | Myung |
| 2022/0159227 A1 | 5/2022 | Quiles Casas |
| 2022/0179209 A1 | 6/2022 | Cherukuri |
| 2022/0192776 A1 | 6/2022 | Gibby et al. |
| 2022/0193453 A1 | 6/2022 | Miyazaki et al. |
| 2022/0201274 A1 | 6/2022 | Achilefu et al. |
| 2022/0245400 A1 | 8/2022 | Siemionow et al. |
| 2022/0245821 A1 | 8/2022 | Ouzounis |
| 2022/0257206 A1 | 8/2022 | Hartley et al. |
| 2022/0269077 A1 | 8/2022 | Adema et al. |
| 2022/0270263 A1 | 8/2022 | Junio |
| 2022/0133484 A1 | 9/2022 | Lang |
| 2022/0287676 A1 | 9/2022 | Steines et al. |
| 2022/0295033 A1 | 9/2022 | Casas |
| 2022/0296315 A1* | 9/2022 | Sokhanvar ............ A61B 34/10 |
| 2022/0304768 A1 | 9/2022 | Elimelech et al. |
| 2022/0351385 A1 | 11/2022 | Finley et al. |
| 2022/0353487 A1 | 11/2022 | Hegyi |
| 2022/0358759 A1 | 11/2022 | Cork et al. |
| 2022/0370152 A1 | 11/2022 | Lavallee et al. |
| 2022/0387130 A1 | 12/2022 | Spaas et al. |
| 2022/0392085 A1 | 12/2022 | Finley et al. |
| 2022/0397750 A1 | 12/2022 | Zhou et al. |
| 2022/0398752 A1 | 12/2022 | Yoon et al. |
| 2022/0398755 A1 | 12/2022 | Herrmann |
| 2022/0405935 A1 | 12/2022 | Flossmann et al. |
| 2023/0004013 A1 | 1/2023 | McCracken et al. |
| 2023/0009793 A1 | 1/2023 | Gera et al. |
| 2023/0025480 A1 | 1/2023 | Kemp et al. |
| 2023/0027801 A1 | 1/2023 | Qian et al. |
| 2023/0032731 A1 | 2/2023 | Hrndler et al. |
| 2023/0034189 A1 | 2/2023 | Gera et al. |
| 2023/0050636 A1 | 2/2023 | Yanof et al. |
| 2023/0053120 A1 | 2/2023 | Jamali et al. |
| 2023/0073041 A1 | 3/2023 | Samadani et al. |
| 2023/0085387 A1 | 3/2023 | Jones et al. |
| 2023/0087783 A1 | 3/2023 | Dulin et al. |
| 2023/0100078 A1 | 3/2023 | Toporek et al. |
| 2023/0123621 A1 | 4/2023 | Joshi et al. |
| 2023/0126207 A1 | 4/2023 | Wang |
| 2023/0129056 A1 | 4/2023 | Hemingway et al. |
| 2023/0131515 A1 | 4/2023 | Oezbek et al. |
| 2023/0149083 A1 | 5/2023 | Lin et al. |
| 2023/0162493 A1 | 5/2023 | Worrell et al. |
| 2023/0165640 A1 | 6/2023 | Dulin et al. |
| 2023/0169659 A1 | 6/2023 | Chen et al. |
| 2023/0196582 A1 | 6/2023 | Grady et al. |
| 2023/0200917 A1 | 6/2023 | Calloway et al. |
| 2023/0236426 A1 | 7/2023 | Manly et al. |
| 2023/0236427 A1 | 7/2023 | Jiannyuh |
| 2023/0260142 A1 | 8/2023 | Chatterjee et al. |
| 2023/0290037 A1 | 9/2023 | Tasse et al. |
| 2023/0295302 A1 | 9/2023 | Bhagavatheeswaran et al. |

(56) References Cited

U.S. PATENT DOCUMENTS

| | | |
|---|---|---|
| 2023/0306590 A1 | 9/2023 | Jazdzyk et al. |
| 2023/0316550 A1 | 10/2023 | Hiasa |
| 2023/0326011 A1 | 10/2023 | Cutforth et al. |
| 2023/0326027 A1 | 10/2023 | Wahrenberg |
| 2023/0329799 A1 | 10/2023 | Gera et al. |
| 2023/0329801 A1 | 10/2023 | Elimelech et al. |
| 2023/0334664 A1 | 10/2023 | Lu et al. |
| 2023/0335261 A1 | 10/2023 | Reicher et al. |
| 2023/0359043 A1 | 11/2023 | Russell |
| 2023/0363832 A1 | 11/2023 | Mosadegh et al. |
| 2023/0371984 A1 | 11/2023 | Leuthardt et al. |
| 2023/0372053 A1 | 11/2023 | Elimelech et al. |
| 2023/0372054 A1 | 11/2023 | Elimelech et al. |
| 2023/0377171 A1 | 11/2023 | Hasler et al. |
| 2023/0377175 A1 | 11/2023 | Seok |
| 2023/0379448 A1 | 11/2023 | Benishti et al. |
| 2023/0379449 A1 | 11/2023 | Benishti et al. |
| 2023/0386022 A1 | 11/2023 | Tan et al. |
| 2023/0386067 A1 | 11/2023 | De et al. |
| 2023/0386153 A1 | 11/2023 | Rybnikov et al. |
| 2023/0394791 A1 | 12/2023 | Wang et al. |
| 2023/0397349 A1 | 12/2023 | Capelli et al. |
| 2023/0397957 A1 | 12/2023 | Crawford et al. |
| 2023/0410445 A1 | 12/2023 | Elimelech et al. |
| 2023/0419496 A1 | 12/2023 | Wuelker et al. |
| 2023/0420114 A1 | 12/2023 | Scholler et al. |
| 2024/0008935 A1 | 1/2024 | Wolf et al. |
| 2024/0016549 A1 | 1/2024 | Johnson et al. |
| 2024/0016572 A1 | 1/2024 | Elimelech et al. |
| 2024/0020831 A1 | 1/2024 | Johnson et al. |
| 2024/0020840 A1 | 1/2024 | Johnson et al. |
| 2024/0020862 A1 | 1/2024 | Johnson et al. |
| 2024/0022704 A1 | 1/2024 | Benishti et al. |
| 2024/0023946 A1 | 1/2024 | Wolf et al. |
| 2024/0041530 A1 | 2/2024 | Lang |
| 2024/0041558 A1 | 2/2024 | Siewerdsen et al. |
| 2024/0045491 A1 | 2/2024 | Sourov |
| 2024/0058064 A1 | 2/2024 | Weiser et al. |
| 2024/0062387 A1 | 2/2024 | Frantz et al. |
| 2024/0103271 A1 | 3/2024 | Zare Seisan |
| 2024/0103282 A1 | 3/2024 | Law et al. |
| 2024/0111163 A1 | 4/2024 | Law et al. |
| 2024/0122560 A1 | 4/2024 | Junio et al. |
| 2024/0126087 A1 | 4/2024 | Gera et al. |
| 2024/0127559 A1 | 4/2024 | Rybnikov et al. |
| 2024/0127578 A1 | 4/2024 | Hiasa |
| 2024/0129451 A1 | 4/2024 | Healy et al. |
| 2024/0130826 A1 | 4/2024 | Elimelech et al. |
| 2024/0134206 A1 | 4/2024 | Gera et al. |
| 2024/0144497 A1 | 5/2024 | Cvetko et al. |
| 2024/0156532 A1 | 5/2024 | Weiman et al. |
| 2024/0177445 A1 | 5/2024 | Galeotti et al. |
| 2024/0177458 A1 | 5/2024 | Zhang et al. |
| 2024/0180634 A1 | 6/2024 | Mikus |
| 2024/0185509 A1 | 6/2024 | Kovler et al. |
| 2024/0202926 A1 | 6/2024 | Crawford et al. |
| 2024/0202927 A1 | 6/2024 | Haslam et al. |
| 2024/0212111 A1 | 6/2024 | Genghi et al. |
| 2024/0261058 A1 | 8/2024 | Gera et al. |
| 2024/0307101 A1 | 9/2024 | Gera et al. |

FOREIGN PATENT DOCUMENTS

| | | |
|---|---|---|
| CN | 101379412 B | 3/2009 |
| CN | 103106348 A | 5/2013 |
| CN | 111915696 A | 11/2020 |
| CN | 112489047 B | 3/2021 |
| DE | 202004011567 U1 | 11/2004 |
| DE | 102004011567 A1 | 9/2005 |
| DE | 102014008153 A1 | 10/2014 |
| DE | 202022103168 U1 | 6/2022 |
| EP | 0933096 A2 | 8/1999 |
| EP | 1640750 A1 | 3/2006 |
| EP | 1757974 A1 | 2/2007 |
| EP | 2119397 A1 | 11/2009 |
| EP | 2557998 A1 | 2/2013 |
| EP | 2823463 A1 | 1/2015 |
| EP | 2868277 A1 | 5/2015 |
| EP | 2134847 B1 | 6/2015 |
| EP | 2963616 A2 | 1/2016 |
| EP | 3028258 A1 | 6/2016 |
| EP | 3037038 A1 | 6/2016 |
| EP | 3069318 A1 | 9/2016 |
| EP | 2891966 B1 | 1/2017 |
| EP | 3121789 A1 | 1/2017 |
| EP | 3123970 A1 | 2/2017 |
| EP | 2654749 B1 | 5/2017 |
| EP | 3175815 A1 | 6/2017 |
| EP | 3216416 A1 | 9/2017 |
| EP | 2032039 B1 | 10/2017 |
| EP | 3247297 A1 | 11/2017 |
| EP | 3256213 A1 | 12/2017 |
| EP | 3306567 A1 | 4/2018 |
| EP | 3320874 A1 | 5/2018 |
| EP | 2030193 B1 | 7/2018 |
| EP | 2225723 B1 | 2/2019 |
| EP | 2619622 B1 | 2/2019 |
| EP | 3034607 B1 | 3/2019 |
| EP | 2892558 B1 | 4/2019 |
| EP | 3494903 A1 | 6/2019 |
| EP | 2635299 B1 | 7/2019 |
| EP | 3505050 A1 | 7/2019 |
| EP | 3224376 B1 | 8/2019 |
| EP | 2875149 B1 | 12/2019 |
| EP | 3206583 B1 | 9/2020 |
| EP | 3711700 A1 | 9/2020 |
| EP | 2625845 B1 | 3/2021 |
| EP | 3076660 B1 | 4/2021 |
| EP | 3858280 B1 | 8/2021 |
| EP | 3593227 B1 | 9/2021 |
| EP | 3913423 A1 | 11/2021 |
| EP | 3789965 B1 | 12/2021 |
| EP | 3634294 B1 | 1/2022 |
| EP | 3952331 A1 | 2/2022 |
| EP | 3960235 A1 | 3/2022 |
| EP | 3635683 B1 | 7/2022 |
| EP | 3602492 B1 | 11/2022 |
| EP | 4173590 A1 | 5/2023 |
| EP | 3533031 B1 | 8/2023 |
| EP | 4252695 A1 | 10/2023 |
| EP | 3195257 B1 | 11/2023 |
| EP | 3405909 B1 | 11/2023 |
| EP | 4270313 A1 | 11/2023 |
| EP | 4287120 A1 | 12/2023 |
| EP | 3488381 B1 | 2/2024 |
| EP | 3834768 B1 | 2/2024 |
| EP | 3903714 B1 | 2/2024 |
| EP | 4336450 A1 | 3/2024 |
| EP | 3814984 B1 | 4/2024 |
| EP | 4115389 B1 | 4/2024 |
| EP | 3752981 B1 | 5/2024 |
| EP | 4375948 A1 | 5/2024 |
| EP | 4383203 A1 | 6/2024 |
| GB | 2507314 A | 4/2014 |
| IL | 262864 A | 3/2019 |
| JP | 2004-237092 A | 8/2004 |
| JP | 2008-507361 A | 3/2008 |
| JP | 2009-514571 A | 4/2009 |
| JP | 2021-525186 A | 9/2021 |
| KR | 20140120155 A | 10/2014 |
| WO | 03034705 A2 | 4/2003 |
| WO | 2007051304 A1 | 5/2007 |
| WO | 2007115826 A2 | 10/2007 |
| WO | 2008103383 A1 | 8/2008 |
| WO | 2010067267 A1 | 6/2010 |
| WO | WO2010074747 A1 | 7/2010 |
| WO | WO2012101286 A1 | 8/2012 |
| WO | 2013112554 A1 | 8/2013 |
| WO | 2014024188 A1 | 2/2014 |
| WO | 2014037953 A2 | 3/2014 |
| WO | 2014113455 A1 | 7/2014 |
| WO | 2014125789 A1 | 8/2014 |
| WO | 2014167563 A1 | 10/2014 |
| WO | 2014174067 A1 | 10/2014 |

(56) References Cited

FOREIGN PATENT DOCUMENTS

| WO | 2015058816 A1 | 4/2015 |
|---|---|---|
| WO | WO2015061752 A1 | 4/2015 |
| WO | WO2015109145 A1 | 7/2015 |
| WO | 2016151506 A1 | 9/2016 |
| WO | 2018/052966 A1 | 3/2018 |
| WO | 2018073452 A1 | 4/2018 |
| WO | WO2018200767 A1 | 4/2018 |
| WO | 2018206086 A1 | 11/2018 |
| WO | 2019/083431 A1 | 5/2019 |
| WO | 2019/135209 A1 | 7/2019 |
| WO | 2019/161477 A1 | 8/2019 |
| WO | 2019195926 A1 | 10/2019 |
| WO | 2019211741 A1 | 11/2019 |
| WO | WO2019210353 A1 | 11/2019 |
| WO | 2020109903 A1 | 6/2020 |
| WO | 2020109904 A1 | 6/2020 |
| WO | 2021019369 A1 | 2/2021 |
| WO | WO2021017019 A1 | 2/2021 |
| WO | WO2021023574 A1 | 2/2021 |
| WO | WO2021046455 A1 | 3/2021 |
| WO | WO2021048158 A1 | 3/2021 |
| WO | WO2021021979 A2 | 4/2021 |
| WO | WO2021061459 A1 | 4/2021 |
| WO | WO2021062375 A1 | 4/2021 |
| WO | WO2021073743 A1 | 4/2021 |
| WO | WO2021087439 A1 | 5/2021 |
| WO | WO2021091980 A1 | 5/2021 |
| WO | 2021255627 A1 | 6/2021 |
| WO | WO2021112918 A1 | 6/2021 |
| WO | 2021130564 A1 | 7/2021 |
| WO | WO2021137752 A1 | 7/2021 |
| WO | WO2021141887 A1 | 7/2021 |
| WO | WO2021145584 A1 | 7/2021 |
| WO | WO2021154076 A1 | 8/2021 |
| WO | 2021/188757 A1 | 9/2021 |
| WO | WO2021183318 A2 | 12/2021 |
| WO | WO2021257897 A1 | 12/2021 |
| WO | WO2021258078 A1 | 12/2021 |
| WO | WO2022009233 A1 | 1/2022 |
| WO | 2022053923 A1 | 3/2022 |
| WO | 2022079565 A1 | 4/2022 |
| WO | 2023/003952 A1 | 1/2023 |
| WO | 2023281395 A1 | 1/2023 |
| WO | 2023/011924 A1 | 2/2023 |
| WO | 2023007418 A1 | 2/2023 |
| WO | 2023021448 A1 | 2/2023 |
| WO | 2023021450 A1 | 2/2023 |
| WO | 2023021451 A1 | 2/2023 |
| WO | 2023/047355 A1 | 3/2023 |
| WO | 2023026229 A1 | 3/2023 |
| WO | 2023/072887 A1 | 5/2023 |
| WO | 2023/088986 A1 | 5/2023 |
| WO | 2023/158878 A1 | 8/2023 |
| WO | 2023/159104 A2 | 8/2023 |
| WO | 2023/161848 A1 | 8/2023 |
| WO | 2023/163933 A1 | 8/2023 |
| WO | 2023/175244 A1 | 9/2023 |
| WO | 2023/186996 A1 | 10/2023 |
| WO | 2023/202909 A1 | 10/2023 |
| WO | 2023/205212 A1 | 10/2023 |
| WO | 2023/205896 A1 | 11/2023 |
| WO | 2023/209014 A1 | 11/2023 |
| WO | 2023/229415 A1 | 11/2023 |
| WO | 2023/232492 A1 | 12/2023 |
| WO | 2023/240912 A1 | 12/2023 |
| WO | 2024/001140 A1 | 1/2024 |
| WO | 2024/002620 A1 | 1/2024 |
| WO | 2024/013642 A2 | 1/2024 |
| WO | 2024/018368 A2 | 1/2024 |
| WO | 2024/046760 A1 | 3/2024 |
| WO | 2024/052136 A1 | 3/2024 |
| WO | 2024/077077 A1 | 4/2024 |
| WO | 2024/121060 A1 | 6/2024 |
| WO | 2024/132609 A1 | 6/2024 |

OTHER PUBLICATIONS

CN Application # 2019800757525 Office Action dated Mar. 1, 2022.
U.S. Appl. No. 16/200,144 Office Action dated Mar. 15, 2022.
U.S. Appl. No. 16/524,258 Office Action dated Apr. 11, 2022.
EP Application # 16767845.7 Office Action dated Apr. 29, 2022.
U.S. Appl. No. 16/419,023 Office Action dated Mar. 1, 2022.
Lorensen et al., "Marching Cubes: A High Resolution 3D Surface Construction Algorithm," ACM SIGGRAPH '87, Computer Graphics, vol. 21, No. 4, pp. 163-169, Jul. 1987.
Wikipedia, "Marching Cubes," pp. 1-4, last edited Sep. 4, 2021.
Milletari et al., "V-Net: fully Convolutional Neural Networks for Volumetric Medical Image Segmentation," arXiv:1606.04797v1, pp. 1-11, Jun. 15, 2016.
Webster (ed.), "Structured Light Techniques and Applications," Wiley Encyclopedia of Electrical and Electronics Engineering, pp. 1-24, year 2016.
Liberadzki et al., "Structured-Light-Based System for Shape Measurement of the Human Body in Motion," Sensors, vol. 18, pp. 1-19, year 2018.
Romero, "Volume Ray Casting Techniques and Applications Using General Purpose Computations on Graphics Processing Units," Thesis/Dissertation Collections, Rochester Institute of Technology, RIT Scholar Works, pp. 1-140, Jun. 2009.
Zhang et al., "Medical Volume Rendering Techniques," Independent Research, Spring 2014, arXiv:1802.07710v1, pp. 1-33, Feb. 21, 2018.
Van Ooijen et al., "Noninvasive Coronary Imaging Using Electron Beam CT: Surface Rendering Versus Volume Rendering," Computers in Radiology, AJR, vol. 180, pp. 223-226, Jan. 2003.
EP Application # 19891059.8 Search Report dated Jul. 27, 2022.
EP Application # 19890849.3 Search Report dated Jul. 27, 2022.
U.S. Appl. No. 16/419,023 Office Action dated Sep. 1, 2022.
U.S. Appl. No. 16/524,258 Office Action dated Oct. 24, 2022.
International Application PCT/IB2022/059030 filed Sep. 23, 2022.
U.S. Appl. No. 16/724,297 Office Action dated Jan. 26, 2021.
U.S. Appl. No. 16/200,144 Office Action dated Dec. 28, 2020.
International Application # PCT/IB2020/060017 Search Report dated Jan. 7, 2021.
U.S. Appl. No. 16/200,144 Office Action dated Aug. 19, 2021.
International Application # PCT/IB2021/055242 Search Report dated Oct. 7, 2021.
U.S. Appl. No. 16/724,297 Office Action dated Nov. 4, 2021.
International Application PCT/IB2022/057965 Search Report dated Dec. 15, 2022.
U.S. Appl. No. 16/524,258 Office Action dated Jan. 24, 2023.
International Application PCT/IB2022/057733 Search Report dated Jan. 26, 2023.
European Application 22203956.2 Search Report dated Feb. 9, 2023.
International Application PCT/IB2022/059030 Search report dated Feb. 28, 2023.
Lumus Ltd., "DK-32 See-through Wearable Display Development Kit" , Rehovot, Israel, pp. 1-2, Dec. 24, 2013.
Liao et al., '3-D Augmented Reality for MRI-Guided Surgery Using Integral Videography Autostereoscopic Image Overlay', IEEE Transactions on Biomedical Engineering, vol. 57, No. 6, pp. 1476-1486, Feb. 17, 2010.
Hainich et al., "Near-Eye displays", Chapter 10 of Displays: Fundamentals and Applications, CRC press, pp. 439-504, Jul. 5, 2011.
Brainlab—Image Registration Options Enhanced Visualization Leveraging More Data , pp. 1-4, Feb. 2019.
Liu et al., "Marker orientation in fiducial registration", Medical Imaging 2003: Image Processing, Proceedings of SPIE vol. 5032, pp. 1176-1185, 2003.
Fingas, "Fraunhofer iPad app guides liver surgery through augmented reality", pp. 1-6, Aug. 22, 2013.
Sagitov et al., "Comparing Fiducial Marker Systems in the Presence of Occlusion", International Conference on Mechanical, System and Control Engineering (ICMSC), pp. 1-6, 2017.
Elimelech et al., U.S. Appl. No. 16/724,297, filed Dec. 22, 2019.
Elimelech et al., U.S. Appl. No. 16/524,258, filed Jul. 22, 2019.
Gera et al., U.S. Appl. No. 16/901,026, filed Jun. 15, 2020.

(56) References Cited

OTHER PUBLICATIONS

International Application PCT/IB2020/056893 Search Report dated Nov. 9, 2020.
Mitrasinovic et al., "Clinical and surgical applications of smart glasses", pp. 381-401, Technology and Health Care, issue 23, year 2015.
Martin-Gonzalez et al., "Head-mounted virtual loupe with sight-based activation for surgical applications", IEEE symposium on mixed and augmented reality, pp. 207-208, Oct. 19-22, 2009.
Figl et al., "A fully automated calibration method for an optical see-through head-mounted operating microscope with variable zoom and focus", pp. 1492-1499, IEEE transactions on medical imaging, vol. 24, No. 11, Nov. 2005.
Medithinq Co. Ltd., "Metascope: world's first wearable scope", pp. 1-7, Jan. 2023.
Martin-Gonzalez et al., "Sight-based magnification system for surgical applications", pp. 26-30, Conference proceedings of Bildverarbeitung für die Medizin, year 2010.
Burstrom et al., "Frameless patient tracking with adhesive optical skin markers for augmented reality surgical navigation in spine surgery", SPINE, vol. 45, No. 22, pp. 1598-1604, year 2020.
Suenaga et al., "Vision-based markerless registration using stereo vision and an augmented reality surgical navigation system: a pilot study", BMC Medical Imaging, pp. 1-11, year 2015.
Mayfield Clinic, "Spinal Fusion: Lateral Lumbar Interbody Fusion (LLIF)", pp. 1-6, Jan. 2021.
Qian et al., "AR-Loupe: Magnified Augmented Reality by Combining an Optical See-Through Head-Mounted Display and a Loupe", pp. 2550-2562, IEEE Transactions on Visualization and Computer Graphics, vol. 28, No. 7, Jul. 2022.
Kazanzides et al., "Systems and Methods for Augmented Reality Magnifying Loupe", case ID 15944, pp. 1-2, Nov. 26, 2020.
JP Application # 2021525186 Office Action dated Dec. 1, 2021.
EP Application # 19796580.9 Search Report dated Dec. 20, 2021.
International Application # PCT/IB2021/058088 Search Report Dec. 20, 2021.
U.S. Appl. No. 16/419,023 Office Action dated Jul. 22, 2021.
16 Augmented Reality Glasses of 2021 (with Features), in Back to News, Dated May 6, 2022, accessed at https://web.archive.org/web/20221127195438/https://circuitstream.com/blog/16-augmented-reality-glasses-of-2021-with-features-breakdowns/.
Everysight, Installing your RX Adaptor, accessed Mar. 13, 2024 at https://support.everysight.com/hc/en-us/articles/115000984571-Installing-your-RX-Adaptor.
Everysight, Raptor User Manual, copyright 2017, in 46 pages.
Frames Direct, InSpatialRx Prescription Insert, Prescription Insert for Magic Leap 1, accessed Mar. 8, 2024 at https://www.framesdirect.com/inspatialrx-prescription-insert.html.
Reddit, Notice on Prescription Lenses for Nreal Glasses, accessed Mar. 13, 2024 at https://www.reddit.com/r/nreal/comments/x1fte5/notice_on_prescription_lenses_for_nreal_glasses/.
Vuzix Blades, Prescription Lens Installation Guide, copyright 2020.
U.S. Appl. No. 15/896,102 U.S. Pat. No. 10,134,166, filed Feb. 14, 2018 Nov. 20, 2018, Combining Video-Based and Optic-Based Augmented Reality in a Near Eye Display.
U.S. Appl. No. 16/159,740 U.S. Pat. No. 10,382,748, filed Oct. 15, 2018 Aug. 13, 2019, Combining Video-Based and Optic-Based Augmented Reality in a Near Eye Display.
U.S. Appl. No. 16/419,023 U.S. Pat. No. 11,570,794, filed May 22, 2019 Sep. 5, 2023, Combining Video-Based and Optic-Based Augmented Reality in a Near Eye Display.
U.S. Appl. No. 18/352,158, filed Jul. 13, 2023, Combining Video-Based and Optic-Based Augmented Reality in a Near Eye Display.
U.S. Appl. No. 18/365,643 U.S. Pat. No. 12,069,233, filed Aug. 4, 2023, Head-Mounted Augmented Reality Near Eye Display Device.
U.S. Appl. No. 18/365,650 U.S. Pat. No. 12,063,345, filed Aug. 4, 2023, Systems for Facilitating Augmented Reality-Assisted Medical Procedures.
U.S. Appl. No. 15/127,423 U.S. Pat. No. 9,928,629, filed Sep. 20, 2016 Mar. 27, 2018, Combining Video-Based and Optic-Based Augmented Reality in a Near Eye Display.
U.S. Appl. No. 16/120,480 U.S. Pat. No. 10,835,296, filed Sep. 4, 2018 Nov. 17, 2020, Spinous Process Clamp.
U.S. Appl. No. 17/067,831, filed Oct. 12, 2020, Spinous Process Clamp.
U.S. Appl. No. 18/030,072, filed Apr. 4, 2023, Spinous Process Clamp.
U.S. Appl. No. 18/365,590 U.S. Pat. No. 11,980,508, filed Aug. 4, 2023 May 14, 2024, Registration of a Fiducial Marker for an Augmented Reality System.
U.S. Appl. No. 18/365,571 U.S. Pat. No. 11,974,887, filed Aug. 4, 2023 May 7, 2024, Registration Marker for an Augmented Reality System.
U.S. Appl. No. 18/632,588, filed Apr. 11, 2024, Registration of a Fiducial Marker for an Augmented Reality System.
U.S. Appl. No. 17/045,766 U.S. Pat. No. 11,980,507, filed Oct. 7, 2020 May 14, 2024, Registration of a Fiducial Marker for an Augmented Reality System.
U.S. Appl. No. 16/199,281 U.S. Pat. No. 10,939,977, filed Nov. 26, 2018 Mar. 9, 2021, Positioning Marker.
U.S. Appl. No. 16/524,258 U.S. Pat. No. 11,980,506, filed Jul. 29, 2019 May 14, 2024, Fiducial Marker.
U.S. Appl. No. 18/631,804, filed Apr. 10, 2024, Fiducial Marker.
U.S. Appl. No. 17/585,629, filed Jan. 27, 2022, Fiducial Marker.
U.S. Appl. No. 16/724,297 U.S. Pat. No. 11,382,712, filed Dec. 22, 2019 Jul. 12, 2022, Mirroring in Image Guided Surgery.
U.S. Appl. No. 17/827,710 U.S. Pat. No. 11,801,115, filed May 29, 2022 Oct. 31, 2023, Mirroring in Image Guided Surgery.
U.S. Appl. No. 18/352,181, filed Jul. 13, 2023, Mirroring in Image Guided Surgery.
U.S. Appl. No. 18/400,739, filed Dec. 29, 2023, Mirroring in Image Guided Surgery.
U.S. Appl. No. 18/780,095, filed Jul. 22, 2024, Mirroring in Image Guided Surgery.
U.S. Appl. No. 16/200,144 U.S. Pat. No. 11,766,296, filed Nov. 26, 2018 Sep. 26, 2023, Tracking System for Image-Guided Surgery.
U.S. Appl. No. 18/470,809 U.S. Pat. No. 11,980,429, filed Sep. 20, 2023 May 14, 2024, Tracking Methods for Image-Guided Surgery.
U.S. Appl. No. 18/631,877, filed Apr. 10, 2024, Tracking Systems and Methods for Image-Guided Surgery.
U.S. Appl. No. 17/015,199, filed Sep. 9, 2020, Universal Tool Adapter.
U.S. Appl. No. 18/598,965, filed Mar. 7, 2024, Universal Tool Adapter for Image Guided Surgery.
U.S. Appl. No. 18/044,380, filed Mar. 8, 2023, Universal Tool Adapter for Image-Guided Surgery.
U.S. Appl. No. 16/901,026 U.S. Pat. No. 11,389,252, filed Jun. 15, 2020 Jul. 19, 2022, Rotating Marker for Image Guided Surgery.
U.S. Appl. No. 18/008,980, filed Dec. 8, 2022, Rotating Marker.
U.S. Appl. No. 17/368,859 U.S. Pat. No. 11,896,445, filed Jul. 7, 2021 Feb. 13, 2024, Iliac Pin and Adapter.
U.S. Appl. No. 18/437,898, filed Feb. 9, 2024, Iliac Pin and Adapter.
U.S. Appl. No. 18/576,516, filed Jan. 4, 2024, Iliac Pin and Adapter.
U.S. Appl. No. 17/388,064, filed Jul. 29, 2021, Rotating Marker and Adapter for Image-Guided Surgery.
U.S. Appl. No. 18/291,731, filed Jan. 24, 2024, Rotating Marker and Adapter for Image-Guided Surgery.
U.S. Appl. No. 18/365,844, filed Aug. 4, 2023, Augmented-Reality Surgical System Using Depth Sensing.
U.S. Appl. No. 18/683,676, filed Feb. 14, 2024, Stereoscopic Display and Digital Loupe for Augmented-Reality Near-Eye Display.
U.S. Appl. No. 18/683,680, filed Feb. 14, 2024, Augmented Reality Assistance for Osteotomy and Discectomy.
U.S. Appl. No. 18/684,756, filed Feb. 19, 2024, Registration and Registration Validation in Image-Guided Surgery.
U.S. Appl. No. 18/693,338, filed Mar. 19, 2024, Surgical Planning and Display.
U.S. Appl. No. 18/365,566, filed Aug. 4, 2023, Systems for Medical Image Visualization.

(56) References Cited

OTHER PUBLICATIONS

U.S. Appl. No. 18/399,253, filed Dec. 28, 2023, Methods for Medical Image Visualization.
U.S. Appl. No. 18/398,837 U.S. Pat. No. 12,044,858, filed Dec. 28, 2023 Jul. 23, 2024, Adjustable Augmented Reality Eyewear for Image-Guided Medical Intervention.
U.S. Appl. No. 18/399,433 U.S. Pat. No. 12,044,856, filed Dec. 28, 2023 Jul. 23, 2024, Configurable Augmented Reality Eyewear for Image-Guided Medical Intervention.
U.S. Appl. No. 18/772,578, filed Jul. 15, 2024, Augmented Reality Eyewear for Image-Guided Medical Intervention.
U.S. Appl. No. 35/508,942 U.S. Pat. No. D. 930,162, filed Feb. 13, 2020 Sep. 7, 2021, Medical Headset.

* cited by examiner

UNIVERSAL TOOL ADAPTER

FIELD OF THE INVENTION

The present invention relates generally to surgery, and specifically to a tool adapter used to hold a tool during the surgery.

BACKGROUND OF THE INVENTION

During surgery, it is often necessary to have a tool used in the surgery held, typically in a relatively fixed position. While the surgeon performing the surgery may hold the tool, having the tool held mechanically frees up the surgeon's hands for other tasks. A number of systems for holding a tool are known in the art.

U.S. Pat. No. 5,441,042 to Putman describes a universal positioning arm employing a clamp having quick disconnect means for releasably holding a surgical instrument such as an endoscope during a surgical procedure. The clamp includes a shaft with a bayonet connector.

U.S. Pat. No. 5,792,046 to Dobrovolny describes a surgical support structure joint which includes a shaft having an axis, a first support member rotatably supported about the axis of the shaft and a camming member coupled to the first support member. The camming member is movable between a first clamped position and a second unclamped position.

U.S. Pat. No. 6,610,009 to Person describes an apparatus for holding a surgical instrument relative to a base. The apparatus has a mounting portion configured and dimensioned to engage a portion of a base, and a jaw assembly including first and second jaw members which define a retaining area configured and dimensioned to retain the shaft of a surgical instrument.

U.S. Pat. No. 6,856,826 to Seeley et al. describes a method for surgical imaging and display including positioning a defined set of markers disposed in a pattern so as cc be imaged in each pose or view of an imaging assembly, the set of markers being fixed in pre-determined positions in a rigid carrier.

U.S. Pat. No. 7,043,961 to Pandey et al. describes how a standard medical or surgical tool's axis is located by attaching to the tool a plurality of location indicating elements or markers having a known geometric or spatial relationship, and placing the tool in a tool calibrator that supports the tool in a manner that allows tools of different diameters to be rotated while maintaining the tool's axis in a fixed or stable orientation.

U.S. Pat. No. 7,229,078 to Lechot describes a surgical tool holder which comprises a shank having a first driveable end and a second coupling end, the second end comprising a coupling device having interfaces for mating with corresponding structures on the inside of a hollow surgical tool.

U.S. Pat. No. 7,320,556 to Vagn-Erik describes a gripping device which comprises a support body within a sleeve, with the sleeve being mounted around the body for relative translational movement along a common axis.

U.S. Pat. No. 7,435,219 to Kim describes a surgical retractor positioning device that creates a surgical working field in a minimally invasive and flexible manner. In one embodiment, the device can include a frame and an arm connected to the frame.

U.S. Pat. No. 7,810,256 to Lakin et al, describes an array for use with a surgical navigation system. The array comprises a frame and first, second and third markers attached to the frame. The first, second and third markers are detectable by a tracking system used in image guided surgery, and the first marker is movable relative to the frame.

U.S. Pat. No. 7,857,271 to Lees describes a surgical tool holder that includes a holding member with a clamping jaw, which is movable between open and clamping positions. A is selectively placed in a rotatable or fixed association with the holding member.

U.S. Pat. No. 7,881,770 to Melkent et al, describes apparatus, for use within an image-guided surgical navigation system, that facilitates the combined positioning and orientation of multiple surgical implements. A tool guide having multiple cannulas is tracked by a surgical navigation system in real time.

U.S. Pat. No. 7,993,353 to Roβner et al. describes a marker system, components and method for use with a medical navigation system, where the marker system includes interchangeable tracking marker holders and fastener bases for attaching the marker holders to instruments or body parts that are to be tracked during a medical procedure.

U.S. Pat. No. 9,149,317 to Arthur et al. describes a device for holding a surgical tool. The device comprises a base extending along a longitudinal axis between a proximal end and a distal end. The distal end is configured for engagement with a body of a patient to stabilize the device.

U.S. Pat. No. 9,179,984 to Teichman et al. describes a navigation system that includes a multi-configuration tracking array that extends from a first medical instrument. A plurality of tracking devices can be positioned on the multi-configuration tracking array.

U.S. Pat. No. 9,532,849 to Anderson et al. describes a robotic surgical system for performing a procedure within a sterile field. The system comprises a manipulator arm and a surgical accessory clamp for coupling a surgical accessory to a distal end portion of the manipulator arm. The accessory clamp includes a base for coupling with the distal end portion of the manipulator arm and two clamp jaws.

U.S. Pat. No. 9,724,165 to Arata et al. describes a surgical system which can identify an interface on an anatomy of a patient. The interface may comprise a painted portion of a bone of the patient, a divot made in the bone, or a mechanical interface that includes a portion configured to be affixed to the bone.

US Patent Application 2016/0256223 to Haimeri et al. describes a data processing method for generating compensation information for tracking or for determining the position and/or orientation of an object in space.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a tool adapter, consisting of:
  an adapter arm having a proximal end terminating with a connection and a distal end having a circular coupling, the circular coupling having a center and defining an axis orthogonal to the circular coupling and passing through the center; and a tool grip rotatingly connected to the circular coupling so as to permit rotation of the tool grip about the axis, the tool grip being configured to fixedly retain a tool along the axis.

In a disclosed embodiment the tool grip includes a collet housed in a collet holder, and the collet is configured on compression to grip the tool. The collet holder may be held by the circular opening, and may be configured to be unable to translate along the axis. The tool adapter may include a collet fastening head configured to screw onto the collet holder so as implement the compression of the collet.

In a further disclosed embodiment the tool adapter includes a position marker fixedly connected to the connection of the proximal end in a preset spatial relationship with the axis, the marker having optical elements enabling the marker to be tracked spatially, so that tracking of the marker provides tracking of the tool retained by the tool grip.

In a yet further disclosed embodiment the tool adapter includes a torque limiting device coupled to the tool grip and configured to apply a preset threshold torque to the grip so that rotation of the tool grip is permitted when the threshold torque is exceeded. The torque limiting device may consist of a plurality of pins retained within the tool grip and configured to exert force against the circular opening.

In an additional disclosed embodiment the tool adapter includes a total indicated runout (TIP) controller coupled to the tool grip and configured to apply a pre-determined TIR to the tool.

There is further provided, according to an embodiment of the present invention, a method for conducting image guided surgery, consisting of:
  providing an adapter arm having a proximal end terminating with a connection and a distal end having a circular coupling, the circular coupling having a center and defining an axis orthogonal to the circular coupling and passing through the center;
  rotatingly connecting a tool grip to the circular coupling so as to permit rotation of the tool grip about the axis, the tool grip being configured to fixedly retain a tool along the axis;
  fixedly connecting a position marker to the connection of the proximal end of the adapter arm in a preset spatial relation ship with the axis, the position marker including optical elements enabling the marker to be tracked spatially, so that tracking of the position marker provides tracking of the tool fixed to the enclosure; and
  presenting an image of the tracked tool to a professional performing the surgery.

The present disclosure will be more fully understood from the following detailed description of the embodiments thereof, taken together with the drawings, in which:

DETAILED DESCRIPTION OF EMBODIMENTS

Overview

During a medical procedure performed using an augmented reality system, a tool used in the procedure, such as a screwdriver used for pedicle screws, typically needs to be tracked, so that images presented to a medical professional using the system correctly register with the tool and with the patient undergoing the procedure. In order to track the tool, a marker is typically connected to the tool, and the marker is tracked by the system. However, in the case of tools such as screwdrivers that need one or more rotations, or even a partial rotation, the marker must stay within the field of view of the tracking system so that tracking is maintained. Furthermore, to eliminate tracking errors, total indicated runout should be minimized.

Embodiments of the present invention provide a solution that overcomes both of these problems by attaching a tool adapter having the marker to the tool, and configuring the tool adapter to be able to rotate about the tool without changing the spatial relationship of the tool to the marker.

The tool adapter comprises an adapter arm which terminates at a proximal end in a connection to the marker, and at a distal end in a circular opening. A tool grip is rotatingly connected to the circular opening so as to permit rotation of the tool grip about an axis defined by the opening, the tool grip being configured to fixedly retain a tool along the axis.

The tool grip typically comprises a collet housed in a collet holder, and the collet is configured to grip the tool when the collet is compressed. Use of a collet firmly and stably holds the tool in a centered location. The collet holder is held in the circular opening, and the combination of the collet, collet holder, and circular opening means that the shaft of the tool remains accurately along the axis of the opening during rotation, and that there is very low total indicated runout (TIR) during all rotations. The inventors have found that in contrast to prior art systems that have a TIR of the order of 100 microns, embodiments of the present invention have a TIR of the order of 10 microns, and thus substantially improve the accuracy of tracking of a gripped tool.

System Description

In the following, all directional references (e.g., upper, lower, upward, downward, left, right, top, bottom, above, below, vertical, and horizontal) are only used for identification purposes to aid the reader's understanding of the present invention, and do not create limitations, particularly as to the position, orientation, or use of embodiments of the invention.

Figure 1:
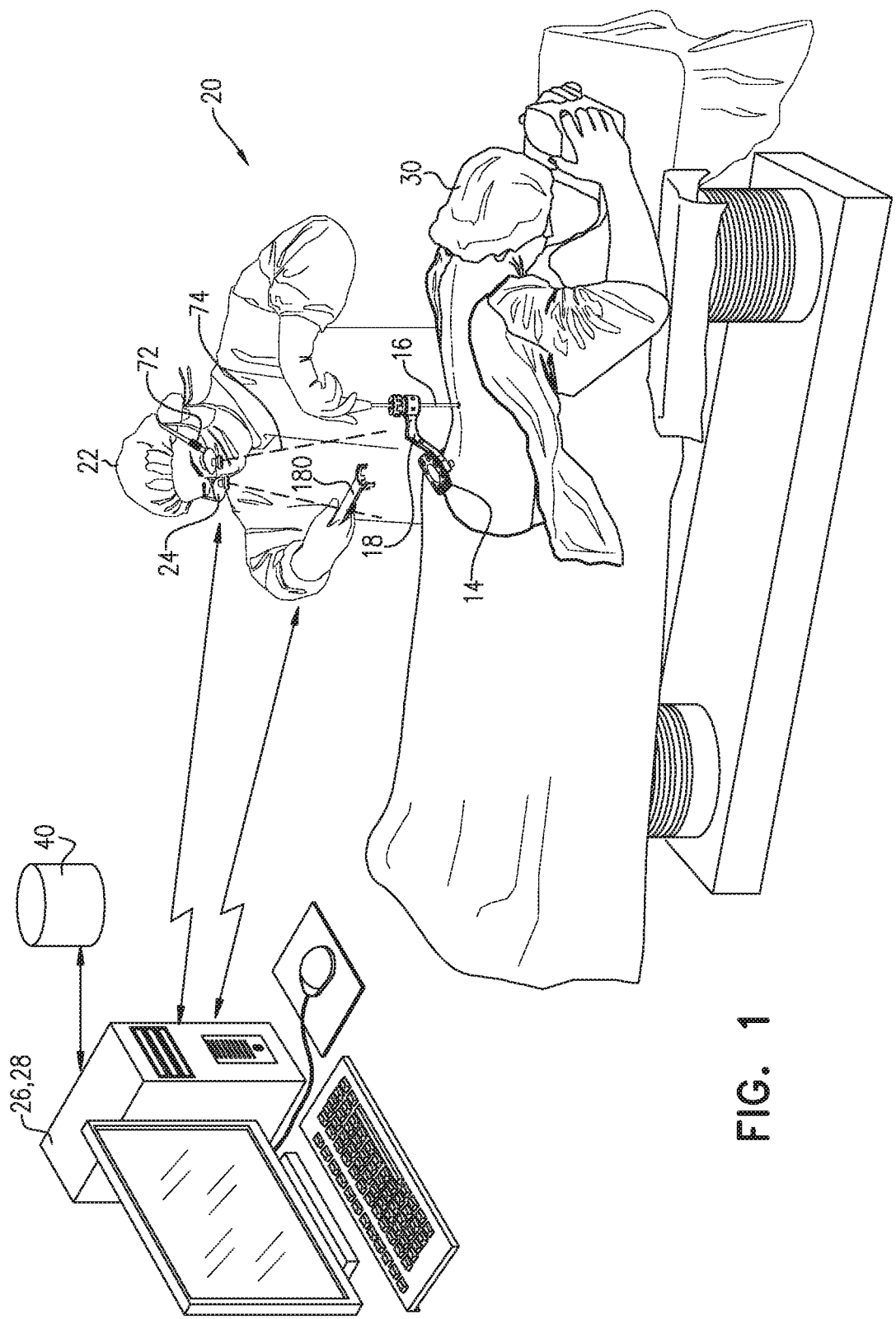
FIG. 1 schematically illustrates use of a tool adapter in an augmented reality system, according to an embodiment of the present invention.

Reference is now made to FIG. 1, which schematically illustrates use of a tool adapter 18 in an augmented reality system 20, according to an embodiment of the present invention. By way of example and for simplicity, in the following description system 20 is assumed to be used by a medical professional 22 in a medical procedure wherein adapter 18 is attached to a cylindrical tool 16, for example a screwdriver, using a wrench 180, as is explained in more detail below. While the description herein assumes a medical procedure, it will be understood that embodiments of the present invention may be used in non-medical situations.

System 20 is operated by medical professional 22, who wears, by way of example, an augmented reality assembly 24, described in more detail below with respect to FIG. 2, which tracks tool adapter 18. It will be understood that assembly 24 is but one type of tracking system, that is able to track the tool holder, and that the scope of the present invention comprises any tracking system able to track tool adapter 18.

Assembly 24 comprises, inter alia, an image capturing device 72, also termed herein a camera 72, that has a field of view 74 and that is configured to capture images in the visible spectrum. Assembly 24 and functions of system 20, processor 26, and device 72 are described below. An assembly similar to augmented reality assembly 24, and its operation, are described in U.S. Pat. No. 9,928,629, to Benishti, et al., whose disclosure is incorporated herein by reference.

While assembly 24 may be incorporated for wearing into a number of different retaining structures on professional 22, in the present description the retaining structure is assumed to be similar to a pair of spectacles. Those having ordinary skill in the augmented reality art will be aware of other possible structures, such as incorporation of the augmented reality assembly into a head-up display that is integrated into a headset worn by the user of system 20, and all such structures are assumed to be comprised within the scope of the present invention.

System 20 comprises and is under overall control of a processor 26. In one embodiment processor 26 is assumed to be incorporated within a stand-alone computer 28, and the processor typically communicates with other elements of the system, including assembly 24, wirelessly, as is illustrated in FIG. 1. Alternatively or additionally, processor 26 may use optical and/or conducting cables for communication. In further alternative embodiments processor 26 is integrated within assembly 24, or in the mounting of the assembly. Processor 26 is typically able to access a database 40, wherein are stored images and other visual elements used by system 20. Software enabling processor 26 to operate system 20 may be downloaded to the processor in electronic form, over a network, for example. Alternatively or additionally, the software may be provided on non-transitory tangible media, such as optical, magnetic, or electronic storage media.

The medical procedure exemplified here is on a patient 30, and during the procedure a position marker 14 is incorporated into tool adapter 18. As described below, marker 14 is trackable by processor 26, so that the processor is able to track also the tool adapter to which the marker is attached, and a tool 16 held by the adapter.

Figure 2:
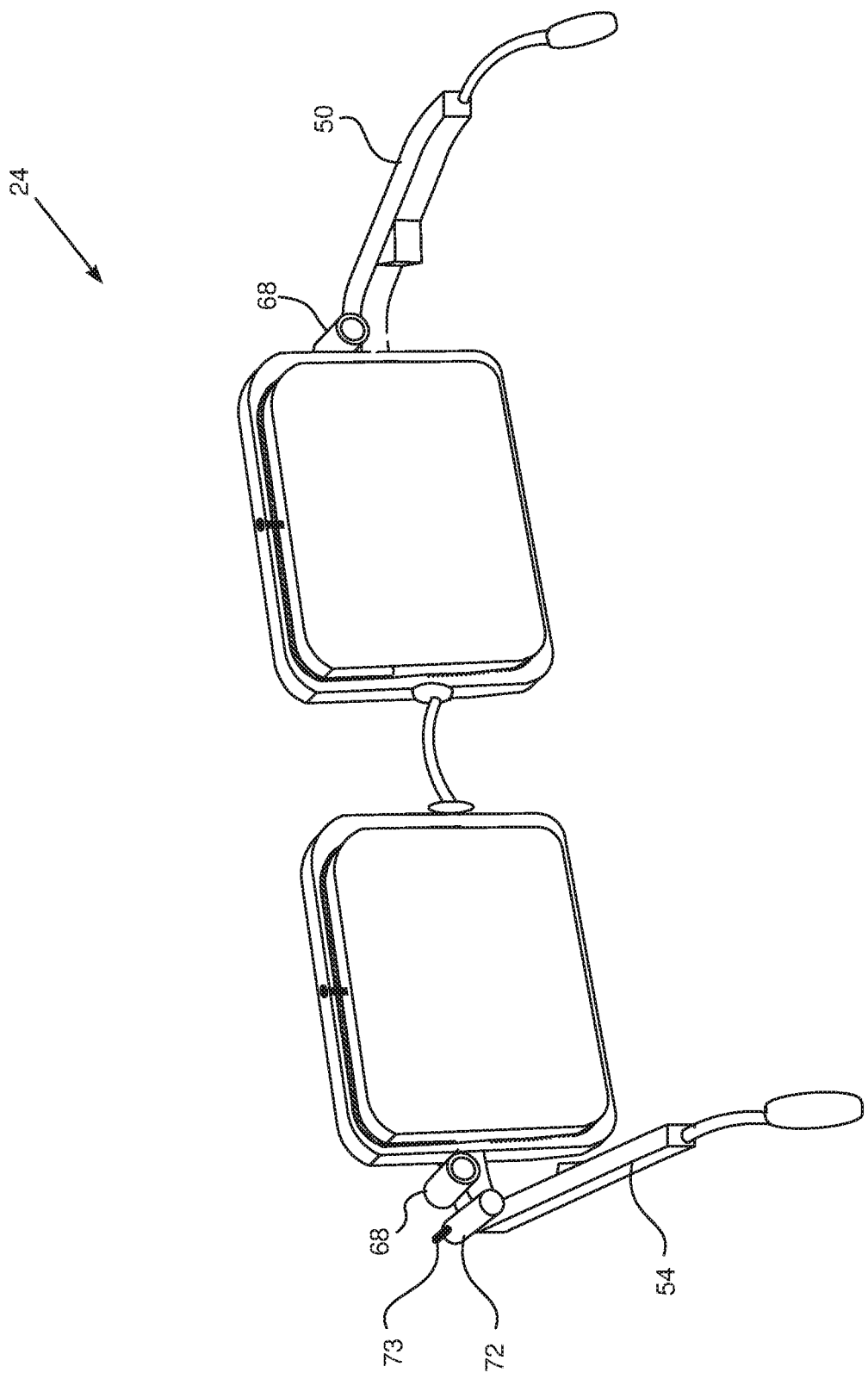
FIG. 2 is a schematic diagram illustrating an assembly, according to an embodiment of the present invention.

FIG. 2 is a schematic diagram illustrating assembly 24, according to an embodiment of the present invention. As stated above, assembly 24 is configured, by way of example, as a pair of spectacles 50 mounted on a frame 54.

At least one image capturing device 68 is attached to frame 54. Typically, devices 68 comprise cameras configured to capture images of scenes viewed by the professional's eyes, including images of marker 14 in the visible spectrum.

As stated above assembly 24 also comprises camera 72, which is configured to capture images of elements of a scene, including marker 14, in front of assembly 24. The images are produced from radiation projected by a projector 73 that is in the spectrum detected by camera 72. Projector 73 is located in close proximity to camera 72, so that radiation from the projector, that has been retroreflected, is captured by camera 72. The camera typically has a bandpass filter configured to block other radiation, such as that projected by surgical lighting. Typically, camera 72 and projector 73 operate in a non-visible region of the spectrum, such as in the near infra-red spectrum. As is described below, at least some retroreflected radiation is typically received from marker 14, and processor 26 uses the image of the marker produced by camera 72 from the received radiation to track the marker, and thus the position and orientation of adapter 18 and of tool 16.

Figure 3:
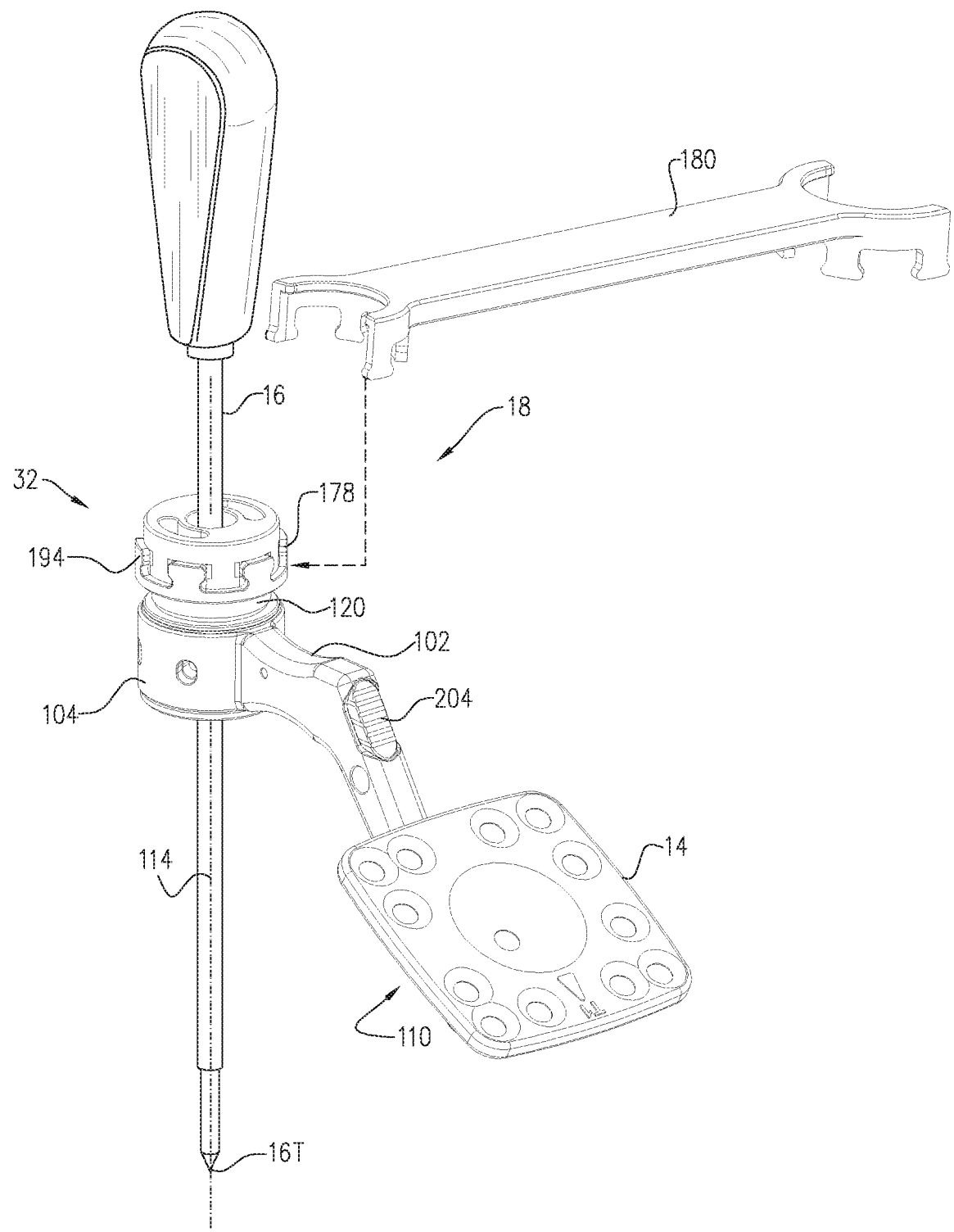
FIG. 3 is a schematic diagram illustrating a tool adapter and a tool, according to an embodiment of the present invention.
Figure 4:
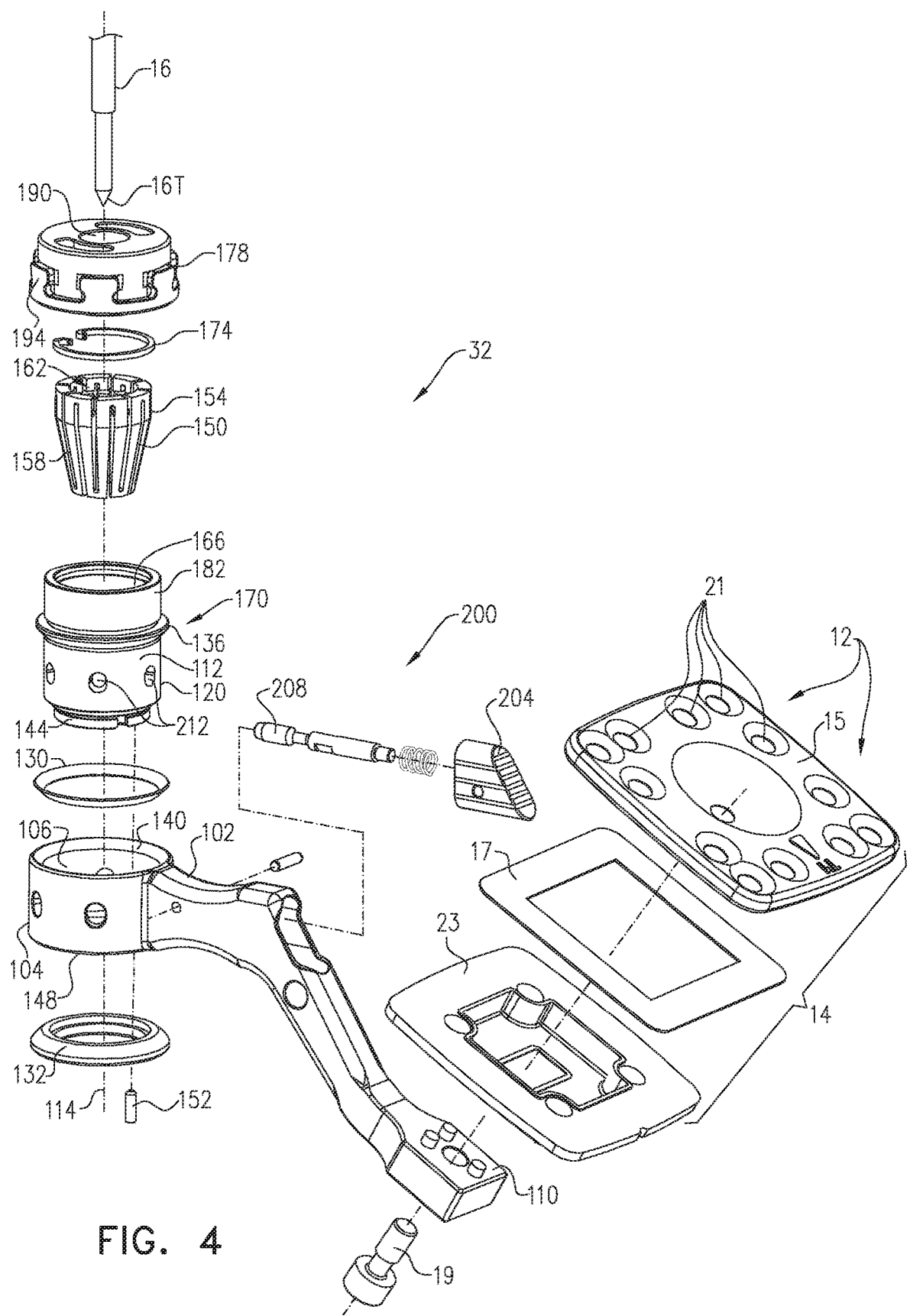
FIG. 4 is a schematic exploded view of the tool adapter and the tool, according to an embodiment of the present invention.
Figure 5:
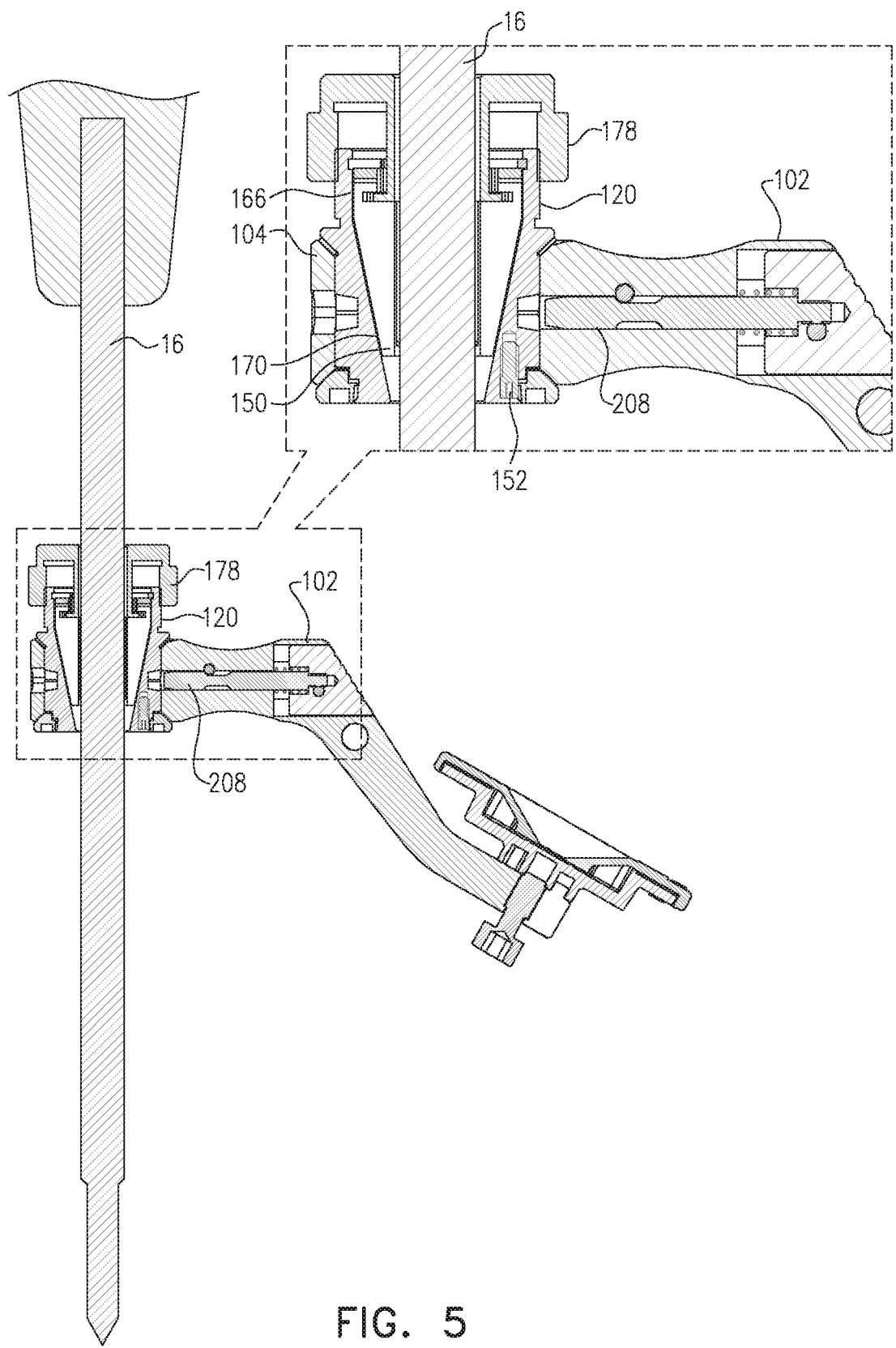
FIG. 5 is a schematic cross-section of the tool adapter and the tool, according to an embodiment of the present invention.

FIG. 3 is a schematic diagram illustrating tool adapter 18 and tool 16, FIG. 4 is a schematic exploded view of the tool adapter and the tool, and FIG. 5 is a schematic cross-section of the tool adapter and the tool, according to an embodiment of the present invention. Tool adapter 18 is formed from an adapter arm 102, which terminates at an upper or distal end of the arm in a circular opening 104, and which terminates at a lower or proximal end of the arm at a connection 110 which fixedly connects the arm to marker 14. A marker similar to marker 14 is described in U.S. patent application Ser. No. 16/199,281 to Messinger et al., which is incorporated herein by reference.

In a disclosed embodiment arm 102 is formed as a single unit. However, in an alternative embodiment arm 102 may be formed as two or more units fixedly connected together. For example, opening 104 may be formed as a separate unit from the remainder of arm 102, and the opening may be fixedly connected by any convenient means to the remainder of the arm.

A tool grip 32 fixedly holds tool 16, as is described in more detail below, and the tool grip is rotatingly connected to circular opening 104, so that tool 16 rotates with respect to the opening as the grip rotates.

Circular opening 104 comprises an internal cylindrical surface 106 having a diameter that is typically in a range 10 mm-50 mm, and the surface defines an axis of symmetry 114 of the opening. Tool Grip 32 comprises a rigid collet holder 120, having an external cylindrical surface 112 with a diameter slightly smaller than that of internal cylindrical surface 106, that fits into opening 104. Except as described below, collet holder 120 is able to freely rotate within opening 104.

After assembling collet holder 120 into opening 104, the holder is held, so that it cannot translate along axis 114, by an upper circular washer 130 and a lower locking nut 132. Locking nut 132 acts as a washer due to its geometry and the material from which it is formed. The washer and nut are typically formed from a low friction material such as PEEK, and act as friction bearings, preventing the holder from translating along axis 114 while allowing the holder to rotate about the axis. Upper washer 130 is held in place between a circular protruding ridge 136 fixedly formed on surface 112 and an upper edge 140 of opening 104.

Lower locking nut 132 is threaded and is configured to mate with a threaded lower region 144 of holder 120, and is dimensioned to mate with a lower edge 148 of opening 104. The lower locking nut is held in place in region 144 by adhesive between the nut and the region, and with a set screw 152 that screws into region 144. Systems other than set screw 152 for holding the locking nut in place, such as a dowel pin, will be familiar to those having ordinary skill in the art, and all such systems are assumed to be comprised within the scope of the present invention.

As is described below, in some embodiments the locking nut may be used to limit, in a controlled manner, the freedom of rotation of arm 102 around collet holder 120.

A collet 150 fits within collet holder 120. Collet 150 has an upper external portion 154 that is cylindrical, and a lower external portion 158 that is conical. Collet 150 also has a central cylindrical aperture 162 that is dimensioned to accept tool 16 when the collet is uncompressed, and to grip the tool when the collet is compressed. An embodiment of the invention comprises a set of collets, each collet of the set being able to accept tools with a range of diameters.

Collet holder 120 has an internal upper cylindrical surface 166 and a lower conical surface 170, the two internal surfaces being dimensioned to mate with the external surfaces of collet 150 (FIG. 5).

Collet 150 is held in place within the collet holder by a retaining spring 174, the retaining spring being sprung against a dedicated groove in upper cylindrical surface 166. A collet fastening head 178 is configured to screw onto a threaded outer surface 182 of collet holder 120. Fastening head 178 is configured internally to mate with spring 174, so that when the head is screwed on surface 182 so as to move towards the collet holder, it pushes on spring 174 and thus pushes and compresses collet 150.

An internal cylindrical tube 190 is fixed to an upper surface of collet fastening head 178, the tube having an internal diameter larger than the external diameter of cylindrical tool 16. An outer surface of fastening head 178 is configured to be able to be gripped by wrench 180 so that the wrench is able to turn the fastening head. By way of example, in one embodiment the outer surface has protuberances 194, and wrench 180 mates with the protuberances so that the wrench is able to rotate the fastening head.

Once tool 16 is positioned within adapter 18, so that it traverses tube 190, rotation of collet fastening head 178 pushes on a flat edge of collet 150 causing the collet to be compressed, and thus to grip tool 16. It will be appreciated that while the tool is gripped by the collet, adapter arm 102 is able to rotate around the tool.

From review of the above description, it will be appreciated that tool grip 32 comprises collet holder 120, and other elements described herein that are connected to the collet holder and collet 150, apart from arm 102 and tool 16.

In some embodiments arm 102 comprises a locking mechanism 200. Mechanism 200 comprises an operating button 204, which is configured to toggle, via a spring and a connecting rod, a pin 208 of the mechanism to mate with or disengage from one of holes 212 in collet holder surface 112. Use of the locking mechanism facilitates attachment of tool 16 to tool adapter 18, by preventing the free rotation of collet holder 120 around the center axis of the tool while wrench 180 rotates fastening head 178.

In some embodiments circular opening 104 has holes that align with holes 212. The holes in opening 104 may be used by professional 22 to align mechanism 200 with holes 212, and may also facilitate flushing of liquids and avoidance of residual liquid when adapter 18 is cleaned.

As stated above marker 14 is fixedly attached to lower-connection 110. In an illustrated embodiment marker 14 comprises optical elements 12 formed on marker 14. Elements 12 may be formed as a plurality of apertures 21 in an upper marker section 15, the apertures being backed by a retroreflective sheet 17 that is held in place with respect to the apertures by a lower marker section 23 fixed to the upper marker section. Marker 14 is fixedly connected by a screw 19 to lower connection 110.

Elements 12 are typically configured to have no rotational or reflective axis of symmetry, so that processor 26 is able to use the image of marker 14, including the images of elements 12 acquired by image capturing device 68 and/or camera 72 of assembly 24, to track the marker, i.e., to determine the location and orientation of the marker in a frame of reference defined by the assembly.

In some embodiments, typically on production of adapter 18, locking nut 132 may be used to limit, in a controlled manner, the freedom of rotation of arm 102 around collet holder 120. In this case the locking nut acts as a torque limiting device. (With no limitation on its rotation, during a procedure professional 22 may inadvertently cause the arm to rotate. While, as described herein, inadvertent rotation of the arm does not affect the functioning of system 20, such rotation may be undesired.)

With no limit on the arm rotation, it will be understood that once tool 16 has been clamped by collet 150 to collet holder 120, and the tool is held horizontal, the weight of arm 102, i.e. the force on the arm due to gravity, will cause the arm to rotate about axis 114 to a vertical "6 o'clock" position. As stated above, locking nut 132 may be adjusted to counteract the force of gravity, so that when tool 16 is held horizontal, arm 102 does not rotate but is also horizontal, in a "3 o'clock" position. The locking nut acts to provide a countervailing torque to the torque generated by gravity. The countervailing torque, herein also termed a threshold torque, does not completely prevent rotation of arm 102, but reduces inadvertent rotation of the arm, since rotation only occurs when the threshold torque is exceeded.

It will be understood that the threshold torque provided by locking nut 132 prevents adapter 18 from rotating due to the force of gravity, but does not apply too much friction that could prevent smooth rotation of tool 16 by professional 22. For an arm and marker having a mass of 80 g, and a center of mass 100 mm from axis 114, the threshold torque applied to arm 192 is approximately 8 N·cm.

In addition to acting as a torque limiting device, locking nut 132 also acts as a controller of the amount of total indicated runout (TIR) of a tool gripped by adapter 18. If locking nut 132 is set to have a threshold torque of 8 N·cm, then the TIR is approximately 60 microns or less.

Figure 6:
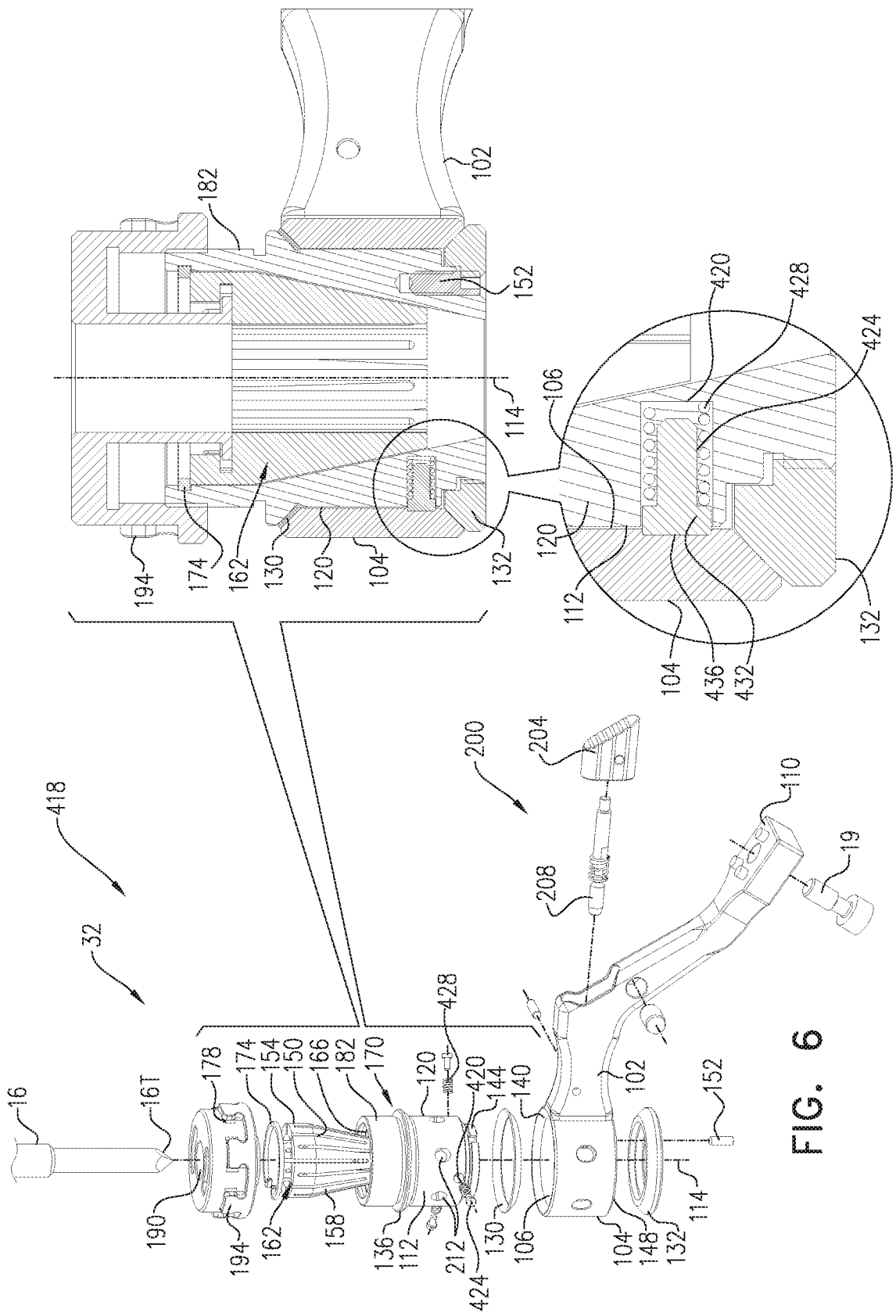
FIG. 6 is a schematic diagram illustrating a tool adapter and a tool, according to an alternative embodiment of the present invention.

FIG. 6 is a schematic diagram illustrating a tool adapter 418 and tool 16, according to an alternative embodiment of the present invention. Apart from the differences described below, the operation of adapter 418 is generally similar to that of adapter 18 (FIGS. 1-5), and elements indicated by the same reference numerals in both adapters 18 and 418 are generally similar in construction and in operation.

In contrast to adapter 18, in adapter 418 three substantially similar blind holes 420 are formed in collet holder 120. Blind holes 420 are distributed symmetrically about axis 114, and are orthogonal to the axis.

Three substantially similar springs 428 are inserted into holes 420, and three substantially similar pins 424 are inserted into the springs. Each pin 424 has a terminal shoulder 432 which has an outer diameter that fits to the diameter of its hole 420.

In addition, the springs and pins are dimensioned so that after insertion each spring lower end contacts the base of its blind hole, the spring upper end contacts shoulder 432, and an exposed surface 436 of the shoulder slightly protrudes from surface 112, as illustrated in FIG. 6.

After assembly of adapter 418, each surface 436 pushes against internal surface 106 of opening 104 with a force that is a function of parameters of spring 428, i.e., the spring constant of the spring as well as its changed length.

The pushing force in turn generates a frictional force on opening 104 when the opening rotates, or attempts to rotate, about axis 114, and the frictional force provides the threshold torque referred to above.

It will be understood that the threshold torque may be set to the value of 8 N·cm cited above, or to a value above or below this value, by selecting a spring with appropriate parameters, as well as by selecting the materials from which pin 424 and opening 104 are formed. Thus, any desired threshold torque may be implemented by these selections, without undue experimentation.

To assemble tool grip 32, springs 428 and pins 424 are first positioned in their blind holes. Opening 104 of the holder arm are then slid over collet holder 120, and over pin shoulders 432. Finally, locking nut 132 is screwed onto holder 120.

In contrast to adapter 18, wherein, as described above, locking nut 132 acts to set values of TIR and the threshold torque, in adapter 418 the two parameters can be set independently. I.e., in adapter 418 locking nut 132 is used to set the value of TIR, and springs 428 and pins 424 are used to set the value of the threshold torque.

The description above assumes that there are three sets of springs 428 and pins 424 distributed symmetrically about axis 114. However, it will be understood that any other convenient plurality of springs and pins distributed symmetrically about the axis, such as two, four, or five springs and pins, may be used as a torque limiting device.

Figure 7:
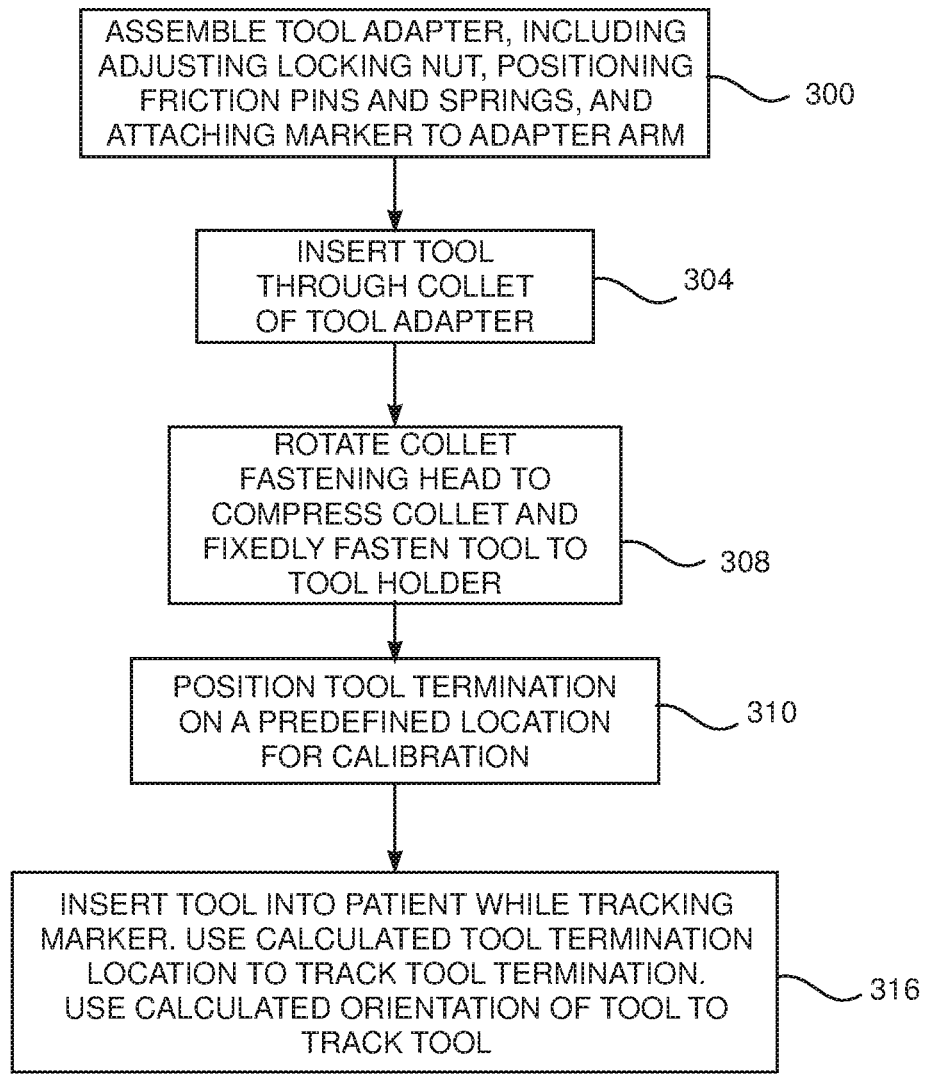
FIG. 7 is a flowchart of steps performed in using a tool adapter with the augmented reality system, according to an embodiment of the present invention.

FIG. 7 is a flowchart of steps performed in using tool adapter 418 with augmented reality system 20 (FIG. 1), according to an embodiment of the present invention. Those having ordinary skill in the art will be able to adapt the description below, mutatis mutandis, for tool adapter 18.

In an initial step 300 tool adapter 418 is assembled, as described above with reference to FIGS. 3, 4, 5 and 6. The assembly typically includes adjusting locking nut 132 to provide a pre-determined TIR, and positioning pins 424 and springs 428 as described above. Also marker 14 is attached to connection 110 of arm 102.

In a tool insertion step 304, cylindrical tool 16 is inserted through aperture 162 of collet 150. Since the tool is to be used in the medical procedure referred to above on patient 30, tool 16 is inserted so that tip 16T of tool 16 is below the level of marker 14.

In a collet activation step 308, wrench 180 is used to rotate collet fastening head 178 so as to compress collet 150, the compression causing the collet to grip tool 16. While wrench 180 is being used, locking mechanism 200 should be activated to lock collet holder 120 in place, as described above, so as to facilitate the compression of collet 150.

As described above, processor 26 is able to track marker 14. Thus, in a calibration step 310, professional 22 positions tool termination 16T on a predefined location, and processor 26 acquires an image of marker 14. From the acquired image, the processor calculates a position of the marker, i.e., its location and orientation, and forms a vector correspondence between the marker position and tool termination 16T and the orientation of tool 16. I.e., the processor "learns" how to translate the marker position to tool termination 16T and to the direction of axis 114. It will be understood that the vector correspondence is unchanged if arm 102 rotates around axis 114, since the marker is fixed to the arm.

In a tool insertion step 316, tool 16 is inserted into patient 30 while processor 26 tracks marker 14. The tracking of the marker provides the processor with the location and orientation, i.e., the marker position, of the marker. From the marker position the processor is able to find, using the vector correspondence found in step 310, the location of tool termination 161 and the orientation of tool 16. The processor is able to use the orientation of tool 16 and the location of tool termination 16T in presenting correctly registered images in assembly 24.

In one embodiment tool 16 comprises a screwdriver, which is inserted into patient 30 so that professional 22 is able to adjust a pedicle screw. It will be appreciated that while the screwdriver is turned, processor 26 is still able to track the screwdriver orientation and its termination, using the vector correspondence found in calibration step 310, so long as marker 14 is tracked.

Alternatively or additionally, during the procedure positioning marker 14 may obstruct the professional's view of the patient, and/or the view of the patient as acquired by devices 68 and/or camera 72. In any of these events, professional 22 may rotate arm 102 about axis 114, applying a torque greater than the threshold torque applied in step 300, so that marker 14 no longer obstructs the view, but while processor 26 continues to track the marker. Since marker 14 continues to be tracked, the processor is able to use the new tracked location of the marker to continue tracking tool 16 and termination 16T of the tool, since the spatial relationships, i.e., the vector correspondence, between the tool and the marker, and between the tool termination and the marker, are unchanged by the tool adapter rotation about axis 114.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A tool adapter, comprising:
an adapter arm having a proximal end terminating with a connection and a distal end comprising a circular opening, the circular opening having a center and defining an axis orthogonal to the circular opening and passing through the center; and
a tool grip comprising a collet configured on compression to grip a tool in order to fixedly retain the tool to the tool grip along the axis, the tool grip being rotatingly connected to the circular opening so as to permit rotation about the axis with respect to the adapter arm of the collet and the tool while the tool is fixedly retained to the tool grip.

2. The tool adapter according to claim 1, wherein the collet comprises an external conical portion, and the tool grip further comprises a collet holder within which the collet is housed, the collet holder comprising an internal conical surface that mates with the external conical portion of the collet so as to implement the compression of the collet responsive to the collet translating along the axis with respect to the collet holder.

3. The tool adapter according to claim 2, wherein the collet holder is held by the circular opening, and is configured to be rotatable about the axis with respect to the circular opening but unable to translate along the axis with respect to the circular opening.

4. The tool adapter according to claim 2, further comprising a collet fastening head configured to screw onto the collet holder so as to translate the collet along the axis with respect to the collet holder to implement the compression of the collet.

5. The tool adapter according to claim 1, wherein the connection of the proximal end is configured to fixedly connect to a position marker, the position marker being in a preset spatial relationship with the axis, and wherein the position marker is configured to be tracked spatially, so that tracking of the position marker provides tracking of the tool retained by the tool grip.

6. The tool adapter according to claim 1, further comprising a torque limiting device coupled to the tool grip and configured to apply a preset threshold torque to the tool grip so that rotation of the tool grip with respect to the adapter arm is permitted when the threshold torque is exceeded.

7. The tool adapter according to claim 6, wherein the torque limiting device comprises a plurality of pins retained within the tool grip and configured to exert force against the circular opening.

8. The tool adapter according to claim 1, further comprising a nut coupled to the tool grip and configured to apply a pre-determined total indicated runout (TIR) to the tool.

9. The tool adapter according to claim 5, wherein the tool is a screwdriver configured to, when fixedly retained to the tool grip, have at least a portion of the tool extending above the tool grip and at least a portion of the tool extending below the tool grip.

10. The tool adapter according to claim 5, further comprising the position marker, wherein the position marker comprises optical elements enabling the position marker to be tracked spatially.

11. The tool adapter according to claim 1, further comprising a locking mechanism configured to selectively prevent rotation of the tool grip with respect to the adapter arm about the axis.

12. A tool adapter, comprising:
an adapter arm extending from a proximal end to a distal end,
the proximal end of the adapter arm being configured to fixedly connect to a position marker, and
the distal end of the adapter arm comprising an opening therethrough, the opening defining an axis orthogonal to the opening; and
a tool grip rotatingly connected to the opening so as to permit rotation of the tool grip with respect to the adapter arm about the axis, the tool grip comprising a collet that is configured to receive a tool so as to fixedly retain the tool with respect to the tool grip along the axis while the collet and the fixedly retained tool are permitted to rotate with respect to the adapter arm about the axis.

13. The tool adapter according to claim 12, wherein the tool grip further comprises a collet holder that houses the collet; and a fastening head configured to force the collet against a conical surface of the collet holder to compress the collet to grip the tool.

14. The tool adapter according to claim 13, wherein at least a portion of the conical surface of the collet holder is positioned within the opening, and the collet holder is configured to be rotatable about the axis with respect to the opening but unable to translate along the axis with respect to the opening.

15. The tool adapter according to claim 12, wherein the proximal end of the adapter arm is configured to maintain the position marker in a preset spatial relationship with the axis, and wherein the position marker is configured to be tracked spatially, so that tracking of the position marker provides tracking of the tool retained by the tool grip.

16. The tool adapter according to claim 12, further comprising a torque limiting device coupled to the tool grip and configured to apply a preset threshold torque to the tool grip so that rotation of the tool grip with respect to the adapter arm is permitted when the threshold torque is exceeded.

17. The tool adapter according to claim 16, wherein the torque limiting device comprises a plurality of pins retained within the tool grip and configured to exert force against the opening.

18. The tool adapter according to claim 12, wherein the tool is configured to, when fixedly retained to the tool grip, have at least a portion of the tool extending above the tool grip and at least a portion of the tool extending below the tool grip.

19. The tool adapter according to claim 12, further comprising the position marker, wherein the position marker comprises optical elements enabling the position marker to be tracked spatially.

20. The tool adapter according to claim 12, further comprising a locking mechanism configured to selectively prevent rotation of the tool grip with respect to the adapter arm about the axis.

21. The tool adapter according to claim 2, wherein at least a portion of the internal conical surface of the collet holder is positioned within the circular opening of the distal end of the adapter arm.

* * * * *